United States Patent
Pallas et al.

(10) Patent No.: US 6,528,295 B2
(45) Date of Patent: Mar. 4, 2003

(54) PROTEIN PHOSPHATASE METHYLESTERASE

(75) Inventors: David C. Pallas, Atlanta, GA (US); Xian X. Du, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/839,497

(22) Filed: Apr. 20, 2001

(65) Prior Publication Data

US 2002/0107374 A1 Aug. 8, 2002

Related U.S. Application Data

(62) Division of application No. 09/293,322, filed on Apr. 16, 1999, now Pat. No. 6,232,110.
(60) Provisional application No. 60/082,202, filed on Apr. 17, 1998.

(51) Int. Cl.$^7$ .......................... C12N 9/16; A61K 38/10
(52) U.S. Cl. ..................... 435/196; 424/185.1; 530/326
(58) Field of Search ..................... 435/196; 424/185.1; 530/324, 325, 326, 327, 328, 329

(56) References Cited

U.S. PATENT DOCUMENTS 6,222,029 B1 * 4/2001 Edwards et al. ............ 536/24.1

OTHER PUBLICATIONS

Brady, L. et al. "A serine protease triad forms the catalytic centre of a triacyglycerol lipase" (1990) *Nature* 343:767–770.
Chen, J. et al. "Tyrosine Phosphorylation of Protein Phosphatase 2A in Response to Growth Stimulation and v–src Transformation of Fibroblasts" (1994) *J. Biol. Chem.* 169:7957–7962.
Chen, J. et al. "Regulation of Protein Serine–Threonine Phosphatase Type–2A by Tyrosine Phosphorylation" (1992) *Science* 257:1261–1264.
Favre, B. et al. "The Catalytic Subunit of Protein Phosphatase 2A Is Carboxyl–methylated *in Vivo* " (1994) *J. Biol. Chem.* 269:16311–16317.
Healy, A.M. et al. "*CDC55* a *Saccharomyces cerevisiae* Gene Involved in Cellular Morphogenesis: Identification, Characterization, and Homology to the B Subunit o Mammalian Type 2A Protein Phosphatase" (1991) *Mol. Cell Biol.* 11:5767–5780.
Hess, J.F. et al. "Phosphorylation of Three Proteins in the Signaling Pathway of Bacterial Chemotaxis" (1998) *Cell* 53:79–87.
Johnston et al. (1994) Science 265:2077–2082.
Kellogg, D.R. et al. "Members of the NAP/SET Family of Proteins Interact Specifically with B–Type Cyclins" (1995) *J. Cell. Biol.* 130:661–673.
Kitakawa et al. (1997) *Eur. J. of Biochem.* 245:449–456.
Kremmer, E. et al. "Separation of PP2A Core Enzyme and Holoenzyme with Monoclonal Antibodies against the Regulatory A Subunit: Abundant Expression of Both Forms in Cells" (1997) *Mol. Cell. Biol.* 17:1692–1701.

Krueger, J.K. et al. "Evidence that the methylesterase of bacterial chemotaxis may be a serine hydrolase" (1992) *Biochem. Biophys. Acta.* 1119:322–326.
Lee, T.H. et al. "INH, a Negative Regulator of MPF, Is a Form of Protein Phosphatase 2A" (1991) *Cell* 64:415–423.
Lee, J. et al. "A specific protein carboxyl methylesterase that demethylates phosphoprotein phosphatase 2A in bovine brain" (1996) *Proc. Natl. Acad. Sci. USA* 93:6043–6047.
Li, M. et al. "Purification and Characterization of Two Potent Heat–Stable Protein Inhibitors of Protein Phosphatase 2A from Bovine Kidney" (1996) *Biochemistry* 34:1988–1996.
Li, M. et al. "Molecular Identification of $I_1{}^{PP2A}$, a Novel Potent Heat–Stable Inhibitor Protein of Protein Phosphatase 2A" (1996) *Biochemistry* 35:6998–7002.
Ogris, E. et al. "Protein phosphatase 2A subunit assembly: the catalytic subunit carboxy terminus is important for binding cellular B subunit but not polyomavirus middle tumor antigen" (1997) *Oncogene* 15:911–917.
Pallas, E.C. et al. "Polyoma Small and Middle T Antigens and SV40 Small t Antigen Form Stable Complexes with Protein Phosphatase 2A" (1990) *Cell* 60:167–176.
Reudiger, R. et al. "Molecular Model of the A Subunit of Protein Phosphatase 2A: Interaction with Other Subunits and Tumor Antigens" (1994) *J. Virol.* 68:123–129.
Rundell, K. "Complete Interaction of Cellular 56,000–and 32,000–$M_r$ Proteins with Simian Virus 40 Small–t Antigen in Productively Infected Cells" (1987) *J. Virol.* 61:1240–1243.
Sontag, E.S. et al. "The Interaction of SV40 Small Tumor Antigen with Protein Phosphatase 2A Stimulates the Map Kinase Pathway and Induces Cell Proliferation" (1993) *Cell* 75:887–897.
Turowski, P. et al. "Differential Methylation and Altered Conformation of Cytoplasmic and Nuclear Forms of Protein Phosphatase 2A During Cell Cycle Progression" (1995) *J. Cell Biol.* 129:397–410.

(List continued on next page.)

*Primary Examiner*—Elizabeth Slobodyansky
(74) *Attorney, Agent, or Firm*—Greenlee, Winner and Sullivan, P.C.

(57) ABSTRACT

Carboxymethylation of proteins is a highly conserved means of regulation in eukaryotic cells. The protein phosphatase 2A (PP2A) catalytic (C) subunit is reversibly methylated at its carboxy-terminus by specific methylesterase. Carboxymethylation affects PP2A activity and varies during the cell cycle. The present disclosure provides the coding sequence of a methylesterase, herein named Protein Phosphatase Methylesterase-1 (PME-1). PME-1 is highly conserved from yeast to human and contains a motif found in lipases, which motif has a catalytic triad-activated serine as the active site nucleophile. Recombinant PME-1 polypeptide produced in bacteria demethylates PP2A C subunit in vitro and okadaic acid, a known inhibitor of the PP2A methylesterase, inhibited this reaction. PME-1 represents the first mammalian protein phosphatase methylesterase cloned to date.

2 Claims, 7 Drawing Sheets

OTHER PUBLICATIONS

Uemura, T. et al. "Mutation of *twins* encoding a regulator of protein phosphatase 2A leads to pattern duplication in *Drosophila* imaginal discs" (1993) *Genes Dev.* 7:429–440.

West, A.H. et al. "Crystal Structure of the Catalytic Domain of the Chemotaxis Receptor Methylesterase, CheB" (1995) *J. Mol. Biol.* 250:276–290.

Winkler, F.K. et al. "Structure of Human Pancreatic Lipase" (1990) *Nature* 343:771–774.

Wylie, D. et al. "Sensory Transduction in Bacterial Chemotaxis Involves Phosphotransfer Between CHE Proteins" (1998) *Biochem. Biophys. Res. Commun.* 151:891–896.

Xie, H. et al. "Protein Phosphatase 2A is Reversibly Modified by Methyl Esterification at its C–terminal Leucine Residue in Bovine Brain" (1994) *J. Biol. Chem.* 269:1981–1984.

Xie, H. et al. "An Enzymatic Activity in Bovine Brain that Catalyzes the Reversal of the C–Terminal Methyl Esterification of Protein Phosphatase 2A" (1994) *Biochem. Biophys. Res. Commun.* 203:1710–1715.

Genbank Accession No. Z19152, Public Availability, Dec. 27, 1992.

Genbank Accession No. U00093, Public Availability, Aug. 4, 1994.

* cited by examiner

PROTEIN PHOSPHATASE METHYLESTERASE

CROSS REFERENCE TO RELATED APPLICATIONS

This application is a divisional application of U.S. application Ser. No. 09/293,322 filed Apr. 16, 1999 now U.S. Pat. No. 6,232,110 and claims priority from U.S. Provisional Application Ser. No. 60/082,202, filed Apr. 17, 1998.

ACKNOWLEDGMENT OF FEDERAL RESEARCH SUPPORT

This invention was made, at least in part, with funding from the United States National Institutes of Health (Grant CA 57327). Accordingly, the United States Government has certain rights in this invention.

BACKGROUND OF THE INVENTION

The field of this invention is the area of molecular biology, and in particular the DNA sequence encoding Protein Phosphatase Methylesterase-1 (PME-1, formerly called p44A), recombinant vectors, and methods for recombinant production of PME-1 demethylase and its use in identifying compositions with inhibitory activity.

Protein phosphatase 2A (PP2A) is a highly conserved serine/threonine phosphatase involved in the regulation of a wide variety of enzymes, signal transduction pathways, and cellular events [Cohen, P. (1989) Annu. Rev. Biochem. 58:453–508; Lee, T. H., et al. (1991) Cell 64:415–423; Mayer-Jaekel, R. E. et al. (1993) Cell 72:621–633; Sontag, E. S. et al. (1993) Cell 75:887–897; Uemura, T. et al. (1993) Genes Dev. 7:429–440]. The minimal structure thought to exist in vivo consists of a heterodimer between a catalytic 36 kDa subunit termed C and a constant regulatory 63 kDa subunit termed A [Kremmer, E. et al. (1997) Mol. Cell Biol. 17:1692–1701; Usui, H. et al. (1988) J. Biol. Chem. 263:3752–3761]. This heterodimer is often further complexed with one of several additional regulatory subunits termed B, B', and B" [Cohen, P. (1989) supra]. In PP2A heterotrimers, the A subunit binds to both the catalytic C and regulatory B-type subunits [Ruediger, R. et al. (1992) J. Virol. 68:123–129; Ruediger, R. et al. (1994) Mol. Cell Biol. 12:4872–4882]. In the case of the B subunit, it has been shown that one or more of the nine C subunit carboxy terminal amino acids are essential for heterotrimer formation [Ogris, E. et al. (1997) Oncogene 15:911–917]. In cells stably transformed by the middle tumor antigen (MT) of polyomavirus, MT is found in place of the B subunit in a small portion (~10%) [Ulug, et al. (1992) J. Virol. 66:1458–1467] of PP2A complexes [Pallas, D. C. et al. (1990) Cell 60:167–176]. MT/PP2A complex formation is important for MT-mediated transformation [Grussenmeyer, et al. (1987) J. Virol. 61:3902–3909; Pallas, et al. (1988) J. Virol. 62:3934–3940; Glenn, G. M. et al. (1995) J. Virol. 69:3729–3736; Campbell, K. S. et al. (1995) J. Virol. 69:3721–3728]. Unlike for B subunit, formation of PP2A heterotrimers containing MT does not require the last nine amino acid residues of the C subunit [Ogris, E. et al. (1997) supra]. The small tumor antigens (STs) of various papovaviruses also form complexes with the A and C subunits of PP2A [Pallas, D. C. et al. (1990) supra].

Consistent with the multiple important roles that PP2A plays in diverse pathways and cellular events, PP2A is highly regulated. The regulatory mechanisms include modulation by regulatory subunits or inhibitory proteins and modulation by post-translational modification of the C subunit. Subunit composition of the PP2A complex affects both catalytic activity and substrate specificity [Agostinis, P. et al. (1992) Eur. J. Biochem. 205:241–248; Favre, B. et al. (1994) J. Biol. Chem. 269:16311–16317; Scheidtmann, K. H. et al. (1991) Mol. Cell. Biol. 11:1996–2003; Sola, M. M. et al. (1991) Biochem. Biophys. Acta 1094:211–216]. In the case of B subunit, changes of up to 100 fold have been documented using cdc2 phosphorylated substrates [Agostinis, P. et al. (1992) Eur. J. Biochem. 205:241–248; Ferrigno, P. et al. (1993) Mol. Biol. Cell 4:669–677; Mayer-Jaekel, R. E. et al. (1994) Journal of Cell Science 107:2609–2618; Ogris, E. et al. (1997) supra; Sola, M. M. et al. (1991) Biochem. Biophys. Acta 1094:211–216]. Two PP2A inhibitor proteins have been reported: I1PP2A (also called PHAPI) and I2PP2A (also called PHAPII or SET) [Li, M. et al. (1996) Biochemistry 34:1988–1996; Li, M. et al. (1996) Biochemistry 35: 6998–7002; Li, M. et al. (1995) J. Biol. Chem. 271:11059–11062]. These also appear to be substrate-dependent in their effects. Perusal of the NCBI GenBank and EST databases via BLAST followed by sequence comparisons using DNASTAR MegAlign software indicates the existence of three different human PHAPI isoforms encoded by different genes and the presence of multiple alternatively spliced forms of PHAPII. A Xenopus homolog of PHAPII was recently shown to interact with B-type cyclins in vitro [Kellogg, D. R. et al. (1995) J. Cell Biol. 130:661–673], but the molecular consequences of this interaction in the regulation of PP2A are not known.

The post-translational modifications of the C subunit that have been reported to modulate PP2A activity include phosphorylation and methylation. Inhibition of PP2A activity in vitro was found upon C subunit phosphorylation at either tyrosine 307 or at one or more unidentified threonine residues [Chen, J. et al. (1992) Science 257:1261–1264; Guo, H. and Damuni, Z. (1993) Proc. Natl. Acad. Sci. USA 90:2500–2504]. A similar modification may occur in vivo in response to transformation or growth stimulation [Chen, J. et al. (1994) J. Biol. Chem. 269:7957–7962]. The first indication that PP2A C subunit was methylated involved two observations. A 36 kDa SV40 small tumor antigen (ST)-associated cellular protein is a major acceptor of the methyl group from radiolabeled S-adenosyl methionine added to cell extracts [Rundell, K (1987) J. Virol. 61:1240–1243]. This ST-associated cellular protein was reported to be the PP2A C subunit [Pallas, D. C. et al. (1990) supra]. The site of methylation of the PP2A C subunit has been identified as leucine 309 [Favre, B. et al. (1994) supra; Lee, J. and Stock, J. (1993) J. Biol. Chem. 268:19192–19195; Xie, H. and Clarke, S. (1994) J. Biol. Chem. 269:1981–1984]. One study reported an approximately two-fold increase in the activity of PP2A upon methylation, adjusting for the stoichiometry of methylation [Favre, B. et al. (1994) supra]. Only phosphorylase a and the peptide substrate, phosphorylated Kemptide, were used in that study. These substrates often give similar results. Thus, it remains to be determined whether greater effects might be observed with other substrates. Based on differential antibody recognition of methylated and non-methylated C subunit, PP2A has been reported to undergo cell cycle dependent changes in methylation [Turowski, P. et al. (1995) J. Cell Biol. 129:397–410]. It is not known whether methylation of PP2A affects the subunit composition of the enzyme. Partially purified fractions of PP2A containing A/C heterodimers or A/B/C heterotrimers have both been shown to be substrates for the PP2A methyltransferase [Xie, H. and Clarke, S. (1994) supra]. There are also data which indicate that methylated C subunit can associate with SV40 ST [Rundell, K. (1987) supra].

The B subunit functions in cell cycle progression through mitosis and in cytokinesis [Healy, A. M. et al. (1991) *Mol. Cell Biol.* 11:5767–5780; Mayer-Jaekel, R. E. et al. (1993) supra; Uemura, T. et al. (1993) *Genes Dev.* 7:429–440]. In cells stably transformed by the middle tumor antigen (MT) of polyomavirus, MT is found in place of the B subunit in a small portion (~10%) [Ulug, E. T. et al. supra] of PP2A complexes [Pallas, D. C. et al. (1990) supra]. MT/PP2A complex formation is known to be important for MT-mediated transformation [Campbell, K. S. et al. (1995) supra; Glenn, G. M. et al. (1995) supra; Grussenmeyer, T. et al. (1987) supra; Pallas, D. C. et al. (1988) supra], but the precise functional consequences of MT association with PP2A are still being elucidated. It was recently shown that there is a requirement for direct B/C subunit interaction to form stable heterotrimers [Ogris, E. et al. (1997) supra].

The nine carboxy-terminal amino acids of the PP2A C subunit, residues 301 to 309, include tyrosine 307, the site of phosphorylation in vitro by v-src, and two potential sites of threonine phosphorylation, residues 301 and 304. Seven of these nine residues, including threonine 304 and tyrosine 307, are found in every PP2A C subunit cloned to date. Threonine 301 is somewhat less conserved.

In order to study cellular proteins which interact with PP2A, two catalytically inactive C subunit mutants were generated and used to form stable complexes. The present invention describes the identification of one of these proteins, herein named Protein Phosphatase Methylesterase-1 (PME-1).

Due to the fact that PP2A is shown to regulate multiple cellular pathways by dephosphorylating several key proteins, there has been a long felt need in the art to understand the molecular mechanisms by which PP2A activity is modulated. The present invention describes cloning of one such modulating enzyme for human PP2A, named herein PME-1, and also shows how to produce recombinant PME-1 polypeptide, which is then used in in vitro assays to identify inhibitors for PME-1 activity.

SUMMARY OF THE INVENTION

It is an object of the present invention to provide nucleotide sequences encoding protein phosphatase methylesterase-1 (PME-1) and the deduced amino acid sequence therefor. Specifically exemplified coding sequences are given in Table 2, together with the deduced amino acid sequence for the human; Tables 6 and 3 for the yeast; Tables 7 and 4 for the nematode. All synonymous coding sequences for the exemplified amino acid sequences are within the scope of the present invention.

It is a further object of the present invention to provide functionally equivalent coding and protein sequences, including equivalent sequences from other mammals and other organisms, including but not limited to yeast and nematodes, and variant sequences from humans. Functionally equivalent PME-1 coding sequences are desirably from about 50% to about 80% nucleotide sequence homology (identity) to the specifically identified PME-1 coding sequence, from about 80% to about 95%, and desirably from about 95% to about 100% identical in coding sequence to the specifically exemplified coding sequence. Each integer and each subset of each specified range is intended within the context of the present invention.

Hybridization conditions of particular stringency provide for the identification of homologs of the human PME-1 coding sequence from other species and the identification of variant human sequences, where those homologs and/or variant sequences have at least (inclusively) 50 to 85%, 85 to 100% nucleotide sequence identity, 90 to 100%, or 95 to 100% nucleotide sequence identity.

The PME-1 coding sequence and methods of the present invention include the homologous coding sequences in organisms other than humans and mice. Methods can be employed to isolate the corresponding coding sequences (for example, from cDNA) from other organisms, including but not limited to other mammals, avian species, Saccharomyces and *Caenorhabditis elegans* useful in the methods of this invention using the sequences disclosed herein and experimental techniques well known to the art.

It will further be understood by those skilled in the art that other nucleic acid sequences besides those disclosed herein for the PME-1 coding sequence will function as coding sequences synonymous with the exemplified coding sequences. Nucleic acid sequences are synonymous if the amino acid sequences encoded by those nucleic acid sequences are the same. The degeneracy of the genetic code is well known to the art. For many amino acids, there is more than one nucleotide triplet which serves as the codon for a particular amino acid, and one of ordinary skill in the art understands nucleotide or codon substitutions which do not affect the amino acid(s) encoded.

Specifically included in this invention are PME-1 sequences from other organisms than those exemplified herein, which sequences hybridize to the PME-1 sequence disclosed under stringent conditions. Stringent conditions refer to conditions understood in the art for a given probe length and nucleotide composition and capable of hybridizing under stringent conditions means annealing to a subject nucleotide sequence, or its complementary strand, under standard conditions (i.e., high temperature and/or low salt content) which tend to disfavor annealing of unrelated sequences. As specifically exemplified, "conditions of high stringency" means hybridization and wash conditions of 65°–68° C., 0.1×SSC and 0.1% SDS (indicating about 95–100% nucleotide sequence identity/similarity). Hybridization assays and conditions are further described in Sambrook et al. (1989) *Molecular Cloning*, Second Edition, Cold Spring Harbor Laboratory, Plainview, N.Y.

As used herein, conditions of moderate (medium) stringency are those with hybridization and wash conditions if 50–65° C., 1×SSC and 0.1% SDS (where a positive hybridization result reflects about 80–95% nucleotide sequence identity). Conditions of low stringency are typically those with hybridization and wash conditions of 40–50° C., 6×SSC and 0.1% SDS (reflecting about 50–80% nucleotide sequence identity).

As used herein, all or part of a nucleotide sequence refers specifically to all continuous nucleotides of a nucleotide sequence, or e.g. 1000 continuous nucleotides, 500 continuous nucleotides, 100 continuous nucleotides, 25 continuous nucleotides, and 15 continuous nucleotides.

Where PME-1-homologous coding sequences are to be isolated from other organisms, one desirably uses nucleotide probes or primers from the most highly conserved regions of the PME-1 protein. For example, the skilled artisan desirably uses hybridization probes or PCR primers encoding the active site region (GHSMGGA, amino acids 154–160, SEQ ID NO:5, in the protein sequence) and a second highly conserved sequence within the protein [GQMQGK, amino acids 333–338, SEQ ID NO:5) to derive probe or primer sequences.

It is well known in the biological arts that certain amino acid substitutions may be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate, and isoleucine and valine, are both pairs of similar amino acids. Similarity between amino acid pairs has been assessed in the art in a number of ways. For example, Dayhoff et al. (1978) in *Atlas of Protein Sequence and Structure*, Volume 5, Supplement 3, Chapter 22, pp. 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

Also within the scope of the present invention are recombinant host cells and recombinant vectors carrying the PME-1 coding sequences of the present invention. Desirably, those coding sequences are operably linked to transcriptional and translational control sequences functional in the host cell into which the vectors are introduced and maintained.

Further provided by the present invention are methods for the recombinant production of a PME-1 protein. After a suitable vector in which a PME-1 coding sequence is operably linked to transcriptional and translational control sequences is introduced into a recombinant host cell of choice, the recombinant host cells are cultured under conditions where the PME-1 sequences are expressed. The PME-1 can then be recovered, if desired. It is understood that the vector and host cells are chosen for maintenance of the vector within the host cell. Similarly, the transcriptional and translational control sequences are chosen for function in the host cell of choice. The specifically exemplified human PME-1 sequence can be modified, for example, using polymerase chain reaction (PCR) technology by substituting synonymous codons according to the known codon usage of the chosen host cell so that expression of the coding sequence is maximized.

DETAILED DESCRIPTION OF THE INVENTION

Figure 1:
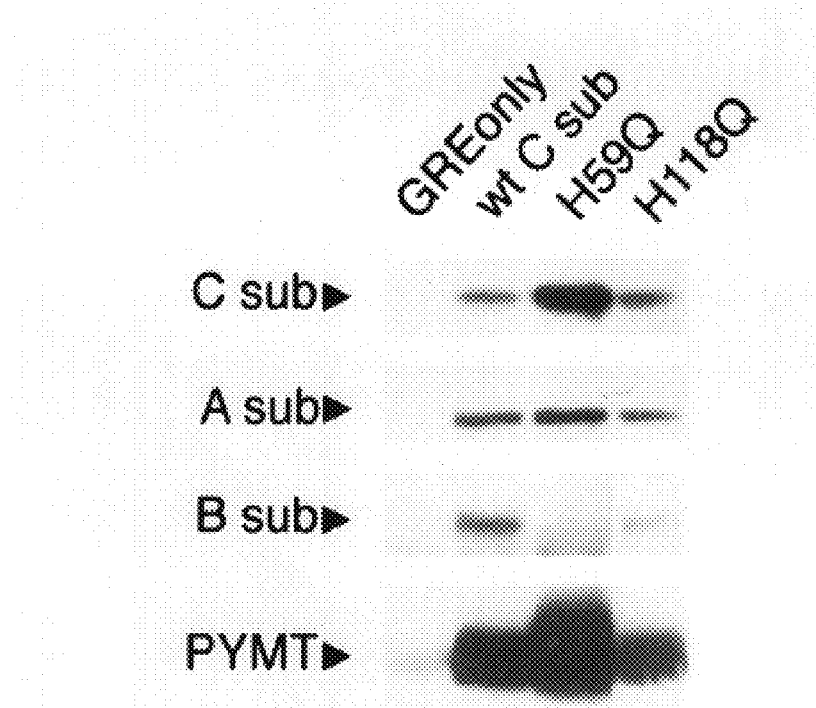
FIG. 1 shows that the catalytically inactive mutants of PP2A can form complexes with the regulatory A subunit and MT in vivo. Lysates from cells containing only control vector (GRE only) or HA-tagged wt (wt-36) or mutant C subunits (H59Q, H118Q) were precipitated with anti-HA tag antibody (12CA5) and analyzed by SDS-PAGE and immunoblotting. The blot was probed first with anti-MT antibody, and then sequentially with antibodies recognizing the A, C (via the epitope tag), and B PP2A subunits. Because a lower level of expression was consistently seen with H118Q, the immunoprecipitate of this mutant was prepared from more cells; to properly control for this, the control immunoprecipitate was prepared from an equivalent amount of cells expressing only the vector. Under these conditions, a small amount of MT binds non-specifically to the immunoprecipitate in the GRE only lane.

"Nucleic acids" and "polynucleotides," as used herein, may be DNA or RNA. One of skill will recognize that the sequences from nematode genes used in the methods of the invention need not be identical and may be substantially identical (as defined below) to sequences disclosed here. In particular, where a polynucleotide sequence is transcribed and translated to produce a functional polypeptide, one of skill in the art recognizes that because of codon degeneracy, a number of synonymous polynucleotide sequences will encode the same polypeptide. Similarly, because amino acid residues share properties with other residues, conservative substitutions of amino acids within a polypeptide may lead to distinct polypeptides with similar or identical function.

The term "operably linked" refers to functional linkage, for example, between a promoter and a downstream sequence, wherein the promoter sequence initiates transcription of the downstream sequence.

"Percentage of sequence identity" for polynucleotides and polypeptides is determined by comparing two optimally aligned sequences over a comparison window, wherein the portion of the polynucleotide or polypeptide sequence in the comparison window may comprise additions or deletions (i.e. gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Gaps introduced to optimize alignment are treated as mismatched, whether introduced in the reference sequence or the comparison sequence. Optimal alignment of sequences for comparison may be conducted by computerized implementation of known algorithms (e.g. GAP, BESTFIT, FASTA, and TFASTA in the Wisconsin Genetics Software Package, Genetics Computer Group (GCG), 575 Science Dr., Madison, Wis., or BlastN and BlastX available from the National Center for Biotechnology Information), or by inspection. Sequences are typically compared using either BlastN or BlastX with default parameters.

Substantial identity of polynucleotide sequences means that a polynucleotide comprises a sequence that has at least 75% sequence identity, preferably at least 80%, more preferably at least 90% and most preferably at least 95%. Typically, two polypeptides are considered to be substantially identical if at least 40%, preferably at least 60%, more preferably at least 90%, and most preferably at least 95% are identical or conservative substitutions. Sequences are preferably compared to a reference sequence using GAP using default parameters.

Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups include but are not limited to: valine-leucine-isoleucine, phenylalanine-tyrosine, lysine-arginine, alanine-valine, asparagine-glutamine, and aspartate-glutamate.

Another indication that polynucleotide sequences are substantially identical is if two molecules selectively hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically stringent conditions for a Southern blot protocol involve washing at 65° C. with 0.2×SSC.

The present inventors have disclosed the full length cDNA encoding human protein phosphatase methylesterase-1, termed PME-1 herein.

Two PP2A C subunit mutants with single amino acid changes in their active site residues were found to form stable complexes with cellular proteins. Mutation of either of two histidines predicted to be in the PP2A C subunit active site results in a stable complex between the mutant C subunit and a protein of 44 kDa. This 44 kDa protein (formerly called p44A) is termed PME-1 herein. Immunoaffinity purification of C subunit/PME-1 complexes generated sufficient protein for microsequencing of HPLC purified PME-1 tryptic peptides. Three of the nine peptide sequences matched a human Expressed Sequence Tag (EST), which the present inventors teach consists of the 3' end of the PME-1 coding region and the entire 3' untranslated sequence. The complete coding region of the human PME-1 cDNA was obtained via an approach involving nested and semi-nested polymerase chain reaction (PCR), utilizing 3' primers corresponding to PME-1 EST sequence and 5' primers corresponding to vector sequence flanking inserts in cDNA libraries. The PME-1 protein was identified as the PP2A methylesterase by several criteria, including molecular size, presence of a motif found in esterases (including lipases) utilizing serine as the nucleophilic catalytic residue, ability of okadaic acid (a known inhibitor of both PP2A and the PP2A methylesterase) to inhibit association of PME-1 with the C subunit mutants and to inhibit PME-1 activity, and finally, activity assays performed in vitro with bacterially expressed protein. Complex formation of PME-1 and mutant C subunit involves, at least in part, the C subunit carboxy terminus. A catalytically inactive C subunit lacking the carboxy-terminal 9 amino acids showed decreased association with the methylesterase, and an antibody specific for the C subunit C-terminus, whose binding is sensitive to mutation of tyrosine 307, interfered with PME-1 binding. Finally, the two mutants that complex with PME-1 do not bind substantial amounts of B subunit. However, two other catalytically inactive mutants that do not bind PME-1 also are deficient in B subunit binding.

The carboxy terminus of the protein phosphatase 2A (PP2A) catalytic (C) subunit is highly conserved. Seven of the last nine residues (301–309) are completely invariant in all known PP2As. Included in these invariant residues are the known $pp60^{c-src}$ phosphorylation site, tyrosine 307, and the known site of methylation, leucine 309. Additionally, one or more of the nine carboxy terminal residues is necessary for formation of PP2A heterotrimers containing the B regulatory subunit. The importance of this tyrosine for binding the methylesterase, the same change in which did not dissociate B subunit, suggests that this is the reason it is so highly conserved.

In order to create catalytically inactive PP2A C subunit mutants that retained maximum structural integrity, single residues likely to be involved in catalysis were mutated conservatively. To identify residues potentially involved in catalysis, an alignment of PP2A and various related phosphatases was performed to identify highly conserved residues. A small number of residues were found that are identical in PP2A, PP1, PPX, PP2B, and PPλ. Of those, two histidines (H) at positions 57 and 118 were chosen as having catalytic potential, and were individually mutated to glutamine (Q), yielding the mutants H57Q and H118Q. Subsequent to the construction of these mutants, the crystal structures of PP1 and PP2B [Goldberg, J. et al. (1995) *Nature* 376:745–753; Kissinger, C. R. et al. (1995) *Nature* 378:641–644] and a mutational analysis of PPλ [Zhuo, S. et al. (1994) *J. Biol. Chem.* 269:26234–26238] were reported, the results of which implicated these two histidines in PP2A catalysis. As described herein below, each C subunit mutant cDNA was constructed with the hemagglutinin (HA) tag at its amino terminus to allow for immunoprecipitation analysis [Ogris, E. et al. (1997) supra]. Individual mutants, wild-type C subunit, or no recombinant C subunit (vector only) were expressed stably in NIH3T3 cell lines with and without coexpression of MT. In the MT expressing cells, most PP2A complexes still contain B subunit because MT is produced at a low level relative to PP2A.

After construction of stable lines, the C subunit mutants were characterized with respect to two properties: 1) ability to form complexes containing the A and B subunits or MT and 2) catalytic activity. To examine complex formation in vivo, immunoprecipitates of epitope-tagged wt and mutant C subunits were probed by immunoblotting for the presence of additional subunits and MT (FIG. 1). Both mutants bind substantial A subunit. H118Q also binds a small amount of B subunit, while H59Q binds almost none of this subunit. Although a small amount of MT was found in control immunoprecipitates, levels of MT well above this were readily detected in the mutant immunoprecipitates, indicating that A/C/MT trilneric complexes had been formed by these proteins. A portion of the MT coimmunoprecipitated with H59Q is shifted relative to the MT associated with wt C subunit; this result is reproducible and will be described in more detail elsewhere. These results indicate that both of these mutants have substantial native structure in vivo.

To test for catalytic activity, phosphatase assays were performed on anti-tag immunoprecipitates from the various cell lines. Using both phosphorylase and histone H1 as substrates, only wt C subunit immunoprecipitates were found to have increased activity as compared to control immunoprecipitates prepared from a cell line containing only "empty" vector (Table 1). Immunoprecipitates of the two mutants showed no activity over background towards either substrate. This finding is consistent with previous published results for mutation of the corresponding residues in related phosphatases.

Figure 2A:
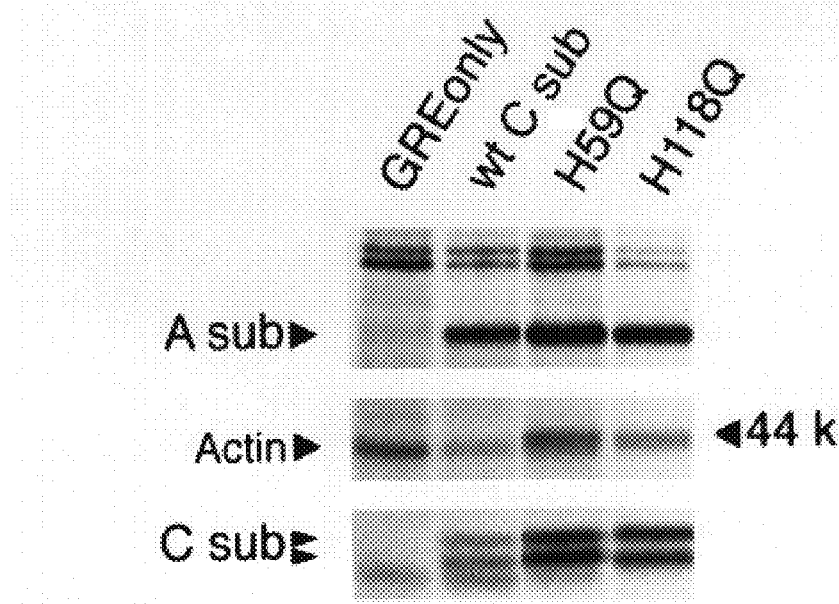
FIG. 2A illustrates HA tag immunoprecipitates prepared from $^{35}$S-labeled cell lines individually expressing HA-tagged wt (36 wt) or mutant C subunits (H59Q, H118Q) or vector only (GRE only) analyzed by SDS-PAGE and autoradiography. Portions of the gel where C subunit, A subunit, and a novel 44 kDa protein migrate are shown. The C subunits migrate as doublets in these gels; whether doublets or a single band are seen varies from gel to gel (compare with FIG. 1). Migration of C subunit as doublets on SDS-PAGE has been noted previously for both HA-tagged and endogenous PP2A C subunits [Campbell et al. (1995) supra; Ogris et al. (1997) supra; Turowski et al. (1995) supra] and does not appear to be due to degradation. The panels and lanes shown are from the same experiment and gel, but the lanes were not all originally adjacent. Even on long exposure, the 44 kDa protein seen in the mutant lanes is not seen in the wt or control lanes.

Catalytically inactive mutants have the potential to form stable complexes with physiological substrates. To determine if novel cellular proteins associated with one or both catalytically inactive C subunit mutants, anti-tag immunoprecipitates were prepared from $^{35}$S-labeled cells. FIG. 2A shows that, in addition to the presence of the C and A subunits, a protein of 44 kDa (p44B) is present in the immunoprecipitates of both catalytically inactive mutants. More p44B appears to associate with H59Q than with H118Q. This protein is not present in immunoprecipitates prepared from either cells expressing wt C subunit or cells containing only "empty" vector. The p44B protein migrates slightly slower than the non-specific actin band which can be seen in all lanes, and actually overlaps the actin bands in this gel. On two-dimensional (2D) gels, however, p44B is completely separated from actin and forms a streak with a pI near 7.

Figure 2B:
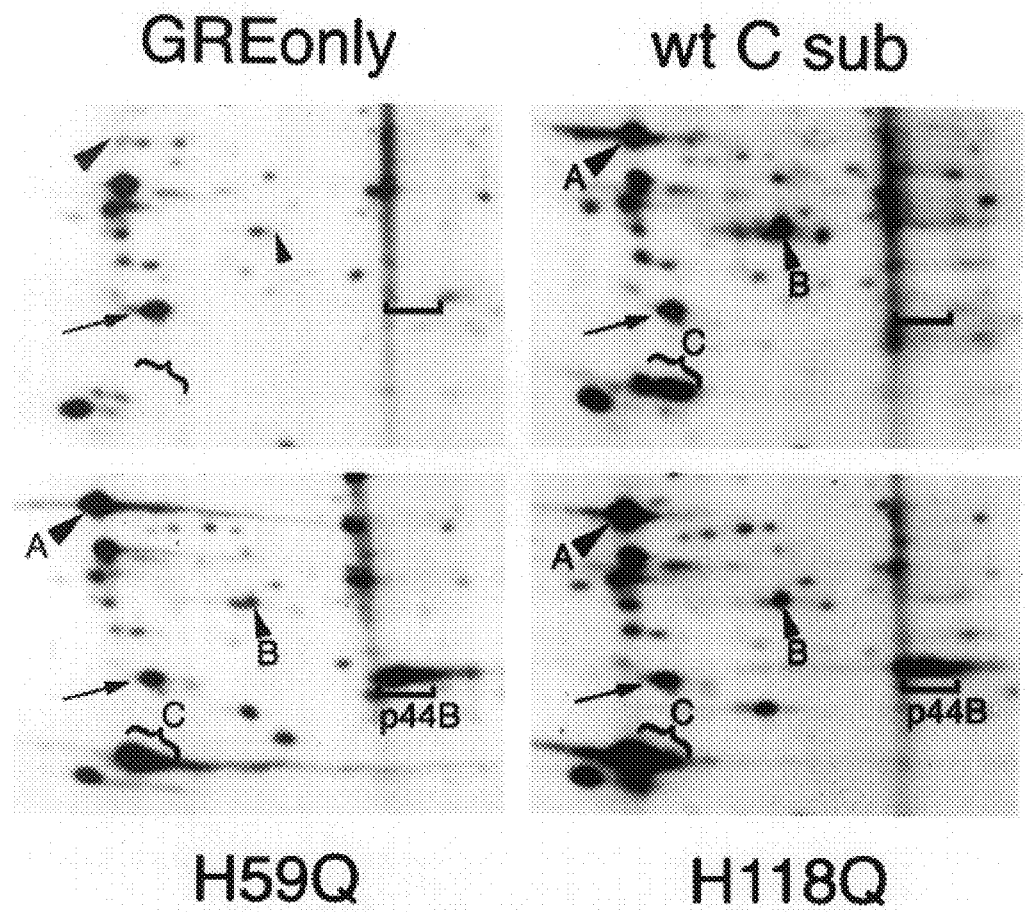
FIG. 2B shows immunoprecipitates identical to those in FIG. 2A analyzed by 2D gel electrophoresis. Only the portion of each gel containing the relevant proteins is shown. The A, B and C subunits and p44B are indicated by labeled brackets and arrowheads, while the corresponding positions in panels lacking these proteins are indicated with unlabeled brackets or arrowheads. For reference, actin is indicated in all panels by a small unlabeled arrow.
Figure 2C:
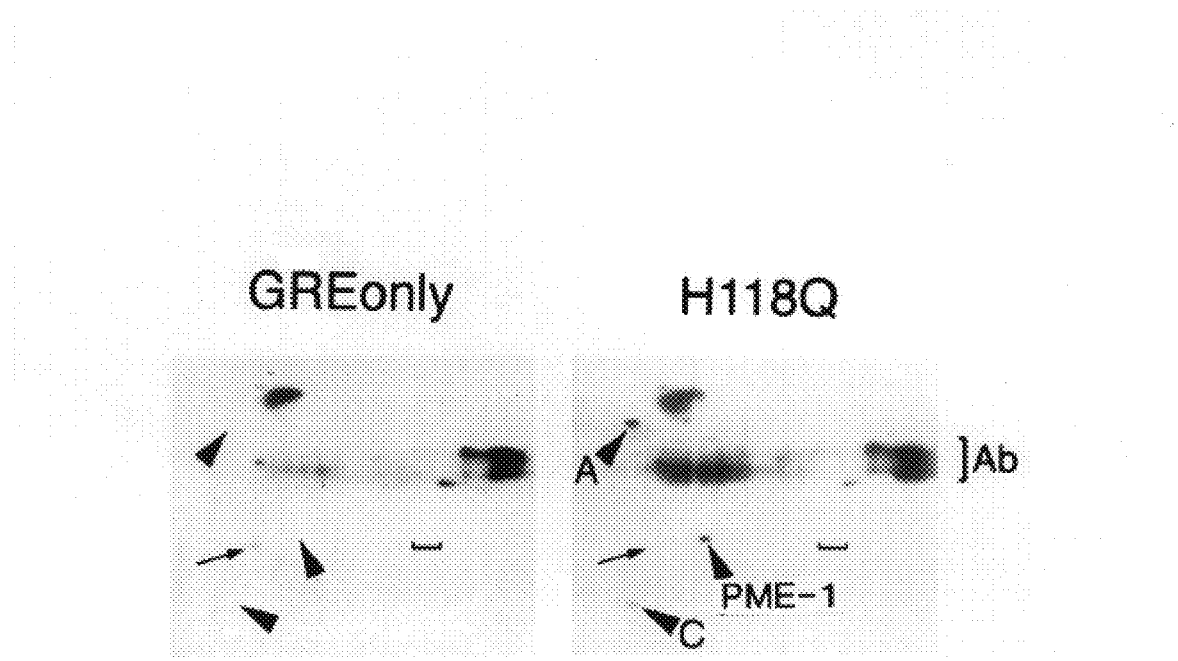
FIG. 2C shows silver-stained 2D gels of HA tag immunoprecipitates prepared from unlabeled cells expressing vector only (GRE only) or the C subunit mutant, H118Q. Only the portion of each gel containing the relevant proteins is shown. The A and C subunits, PME-1, and anti-HA tag antibody heavy chain (Ab) are indicated by labeled brackets and arrowheads. Unlabeled arrowheads indicate the corresponding positions in the GRE only control panel. For reference, actin is indicated in both panels by a small unlabeled arrow. The approximate position that p44B would be located on these gels is indicated by the unlabeled brackets.

In order to see if sufficient p44B could be obtained to facilitate microsequencing, scaled up immunoprecipitates were analyzed on 2D gels and silver-stained. FIG. 2C shows silver-stained 2D gels of immunoprecipitates from vector only control cells (GRE only) and from cells expressing H118Q. P44B was not readily visible in these gels (see brackets); however, another 44 kDa protein was seen that also specifically coimmunoprecipitates with H118Q. This protein, now designated PME-1, was present in almost a 1:1 stoichiometry with the A and C subunits and was formerly called p44a because its pI, approximately 6, was more acidic than that of p44B. A similar PME-1 spot was found in silver-stained immunoprecipitates of H59Q. Comparison of the H118Q panels in FIG. 2C and FIG. 2B fails to reveal an $^{35}$S-labeled spot corresponding to PME-1, suggesting that PME-1 probably has a much longer half-life than the PP2A C or A subunits or p44B.

To facilitate cloning of the nucleotide sequence encoding PME-1, sufficient PME-1 protein for microsequencing was obtained by purifying epitope-tagged H59Q complexes on an anti-tag immunoaffinity column as described hereinbelow. Because PME-1 migrated close to actin on standard 10% SDS-PAGE, the separation of these two proteins was optimized empirically, resulting in the use of a lower percent acrylamide electrophoresed for an extended period of time. Proteins in the gel were electrophoretically transferred to PVDF membrane and visualized by staining with Ponceau S. Both the actin and a clearly separated 44 kDa band migrating just above it were excised for further processing. Microsequencing of a tryptic peptide from the lower band confirmed that it was indeed actin. Nine microsequences obtained from the 44 kDa band matched no known protein in GenBank, indicating that it was a novel protein. However, a human EST sequence (H12112) was found deposited that matched three of the partial sequences obtained from the 44 kDa protein. In addition, homologous sequences were found in *Caenorhabitis elegans* cosmids, and a single *Saccharomyces cerevisiae* homolog was identified. Additional DNA sequencing of this EST revealed coding information for two more PME-1 microsequences, and it was determined that H12112 encoded most of the carboxy-terminal half of the PME-1 protein (162 amino acids). Because the EST came from an oligo dT-primed cDNA library, it likely contains the entire 3' untranslated region (UTR).

To obtain the missing 5' portion of the coding region, nested and seminested PCR was performed as described in the Examples hereinbelow. 5' primers corresponded to vector sequence that flanked cDNA inserts in the library being used as template, and 3' primers corresponded to known sequence (EST or newly derived 5' sequence). In this manner, the remainder of the coding region and a portion of the 5' UTR were obtained. Because of the possibility of PCR errors during the multiple reamplification reactions that were necessary to obtain the complete cDNA, the sequences of selected portions of the cDNA sequence were verified. For this purpose, RT-PCR was performed with 5' and 3' UTR primer sequences to generate directly from HeLa cell MRNA a product containing the entire coding region and much of the 5' UTR. The final cDNA sequence is shown in Table 2.

Figure 3A:
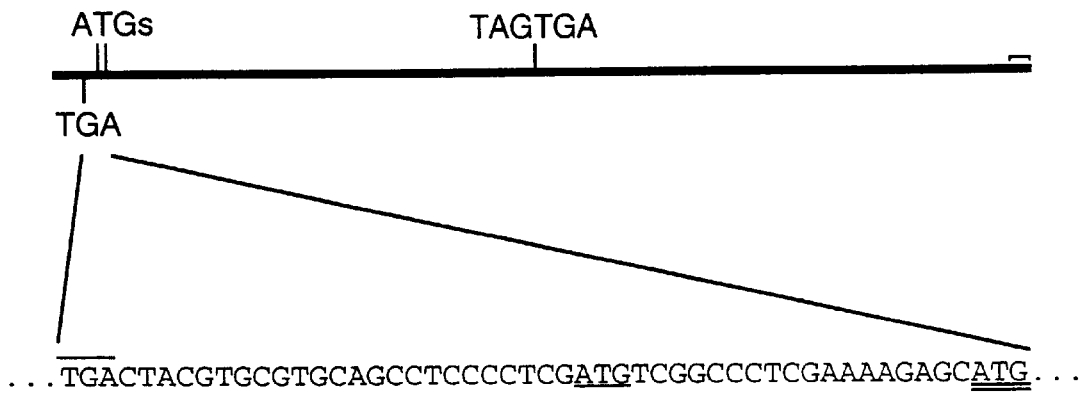
FIG. 3A is a schematic of a 2.5 kb human PME-1 cDNA. On the stick diagram, the positions of the in frame 5' UTR stop codon (TGA), of the first two potential start codons (ATGs), of tandem stop codons (TAGTGA) at the end of the PME-1 ORF, and of the poly A tail (bracket) are shown. The 3' end of the 3' UTR, including the position of the poly A tail, was deduced by analyzing overlapping PME-1 ESTs; all other regions were directly sequenced. The sequence shown extends from the in frame 5' UTR stop codon (TGA; overlined) to the second possible start ATG (double underlined) (SEQ ID NO: 16). The first possible start ATG (underlined once in the sequence shown) was identified as the authentic start site in vivo by making constructs whose transcription/translation products in vitro would start with one or the other of these two ATGs. $^{35}$S-labeled in vitro transcription/translation product starting at the first ATG, but not the product starting at the second ATG, comigrated precisely on 2D gels with PME-1 from HeLa cell lysates.
Figure 3B:
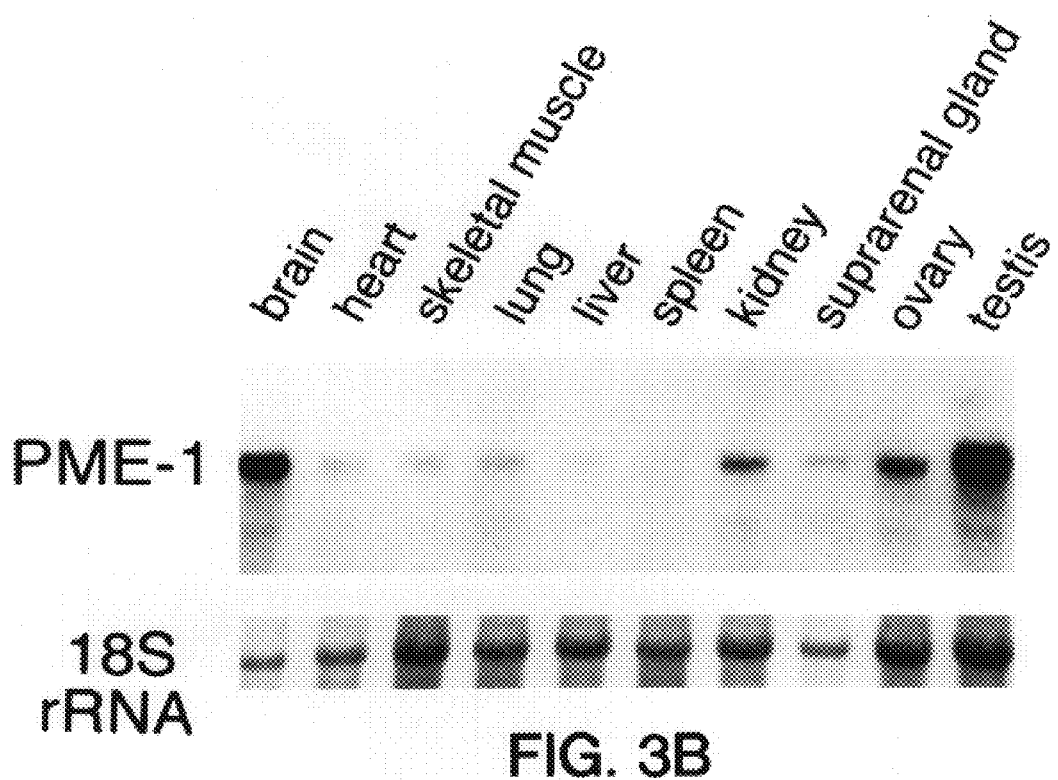
FIG. 3B shows that PME-1 mRNA is expressed in different tissues. Total RNA from the indicated mouse organs was separated by electrophoresis and hybridized with a mouse PME-1 partial cDNA probe from the 3' UTR of mouse PME-1. In a separate experiment, the size of the PME-1 transcript was calculated to be 2.6±0.2 kB. The lower panel shows the 18S rRNA from the same blot visualized with methylene blue.

A schematic of a PME-1 cDNA that includes the end of the 3' UTR deduced from overlapping ESTs is shown in FIG. 3A. The complete cDNA is approximately 2500 nucleotides in length, including an 1164 nucleotide region (including tandem stop codons) encoding a protein of 386 amino acids and a predicted pI of 5.8. All nine tryptic peptide microsequences obtained from the purified 44 kDa band are found encoded in the cloned coding sequence throughout its length (underlined in Table 2), confirming that this is the cDNA for the purified 44 kDa associated protein. This result is also consistent with the reading frame being correct throughout. There is an in frame stop codon a short distance 5' of the first ATG that was verified in the RT-PCR product, so (without wishing to be bound by theory), we believe there is no missing 5' coding sequence. In addition, the entire coding sequence, including the positions of the stop codon(s), has been verified several times. Over 98 % of the microsequenced murine residues (107 of 109) were identical to the human sequence. The double underlined serine at position 42 corresponds to a threonine in murine PME-1. When a probe specific for mouse PME-1 was used to detect transcripts from different mouse organs, a single transcript of _2.6 Kb was detected in all tissues (FIG. 3B). To date, multiple ESTs have been deposited which encode portions of PME-1. These sequences separately cover the entire 3' and 5' UTRs, but not the entire coding region, and there is no association between the EST sequences and the function of the encoded protein. Information from the NCBI Cancer Genome Anatomy Project (CGAP) indicates that PME-1 ESTs have been mapped to human chromosome 11, interval D1S916-D11S911 (80–84 cM). It is not known at this time whether PME-1 is mutated in any of the diseases with defects mapped to this general region of chromosome 11.

The 386 amino acid PME-1 protein product encoded by the human PME-1 cDNA ORF is shown in Table 2. It has a pI of 5.8, consistent with its migration on 2D gels like the one shown in FIG. 2C. All nine mouse PME-1 tryptic peptide sequences (underlined in Table 2) were accounted for in the human sequence with differences present only at a few positions, indicating that PME-1 is well conserved between these two species. Using the NCBI BLAST program, highly homologous sequences probably corresponding to PME-1 homologs were found for zebrafish, for *C. elegans*, and for *S. cerevisiae*. The hypothetical 88.4 kDa *C. elegans* protein in chromosome 3, B0464.7, contains some of the *C. elegans* sequence homologous to PME-1, but lacks other highly homologous sequences, suggesting that it may represent an inaccurate prediction of exon combinations. A more likely combination of exons that includes all B0464 cosmid exons homologous to PME-1 generates a protein of 365 amino acids and approximately 40 kDa (Table 2). S. cerevisiae PME-1 (Table 9, Table 3) appears to be a single hypothetical 44.9 kDa protein (PIR accession number S46814; SwissProt accession number P38796) of unknown function encoded by an ORF on chromosome 8R (YHN5; GenBank accession number U10556). Recently YHN5 was proposed to be a mitochondrial ribosome subunit protein and named YmS2, based on a single partially homologous nonapeptide sequence [Kitakawa, M. et al. (1997) Eur. J. Biochem. 245:449–456]. Human PME-1 has approximately 40% and 26% respective amino acid identity with the C. elegans and yeast sequences (Table 9). A highly charged stretch of amino acids is present in human PME-1 but absent in PMEs from C. elegans and S. cerevisiae. This stretch of amino acids does not represent a cloning artifact, because 2D gel comigration experiments showed that $^{35}$S-labeled PME-1 in vitro transcription/translation product comigrated precisely on 2D gels with PME-1 from HeLa cell lysates.

Figure 4:
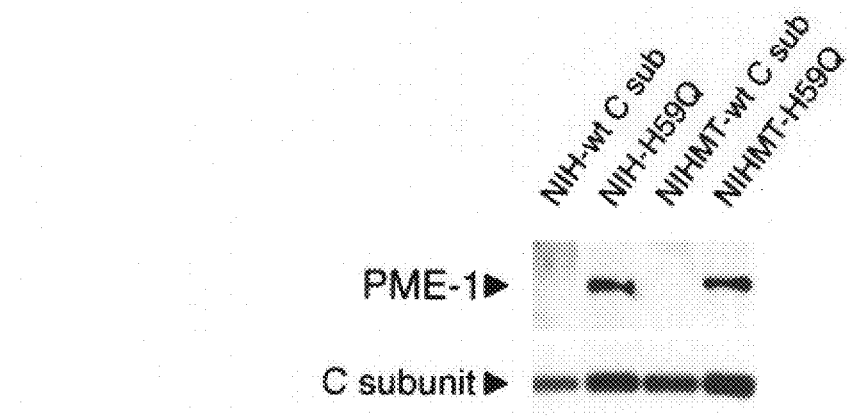
FIG. 4 demonstrates that PME-1 stably associates with H59Q but not wild-type C subunit. HA tag immunoprecipitates prepared from NIH3T3 (NIH) or MT-transformed NIH3T3 (NIHMT) cell lines individually expressing HA-tagged wt (wt C sub) or mutant (H59Q) C subunits were analyzed by SDS-PAGE and immunoblotting with HA tag antibody and PME-1 anti-peptide antibody. The C subunits migrate as tight doublets in these gels. The panels and lanes shown are from the same experiment and gel, but the lanes were not all originally adjacent. Even on long exposure, the 44 kDa protein seen in the mutant lanes is not seen in the wt lanes.

In order to facilitate further experiments characterizing PME-1, an anti-PME-1 peptide antibody was raised to a sixteen amino acid peptide sequence encoded by the PME-1 cDNA. This peptide antibody detected a 44 kDa protein present in H59Q immunoprecipitates, but absent from immunoprecipitates of wild-type C subunit (FIG. 4). Thus, PME-1, like p44B, associates stably with the catalytically inactive mutant C subunits, but not with wt C subunit. Because B subunit, but not MT, requires the C subunit carboxy-terminus for association with the PP2A A/C heterodimer, we wanted to determine if MT expression might increase the amount of PME-1 bound to H59Q. Similar levels of PME-1 were coimmunoprecipitated from untransformed NIH3T3 cells and polyomavirus MT-transformed NIH3T3 cells (FIG. 4), indicating that MT expression does not greatly affect the level of H59Q/PME-1 complex formation in the cell.

When the human, C. elegans, and S. cerevisiae PME-1 protein sequences were analyzed for motifs found in the Prosite database using DNASTAR Lasergene software, a consensus sequence ([LIV]-x-[LIVFY]-[LIVST]-G-[HYWV]-S-x-G-[GSTAC]) (SEQ ID NO: 15) for lipases utilizing an active site serine was found to be conserved. The invariant serine in this motif, corresponding to serine 156 in human PME-1, is the active site serine in these enzymes. In addition, scattered similarities can be seen between other regions of the PME-1 sequence and some of the lipases that have this motif. Therefore, PME-1 is probably a lipase whose active site serine is serine 156.

The various lipases that share this motif are found in both prokaryotes and eukaryotes and include, among others, two D. melanogaster carboxylesterases. In addition, CheB, a bacterial glutamate methylesterase, has a similar, but not identical, sequence surrounding its active site serine [Krueger, J. K. et al. (1992) Biochim. Biophys. Acta. 1119:332–326] (Table 8). CheB [West, A. H. et al. (1995) J. Mol. Biol. 250:276–290] and other lipases utilizing an active site serine [e.g. Winkler, F. K. et al. (1990) Nature 343:771–774; Brady, L., et al. (1990) Nature 343:767–770] have a catalytic triad in their primary sequence in the order Ser-Asp(or Glu)-His. Of the conserved histidines in human PME-1, His 349 is a likely candidate for a putative catalytic triad histidine (Table 9). Identification of a putative PME-1 catalytic triad acidic residue by sequence comparison is more problematic because there are multiple acidic residues conserved between species. However, of these, two aspartates in human PME-1, Asp 181 and Asp 324, show conservation in position with putative catalytic triad aspartates in other lipases, and therefore may be more likely possibilities.

Figure 5:
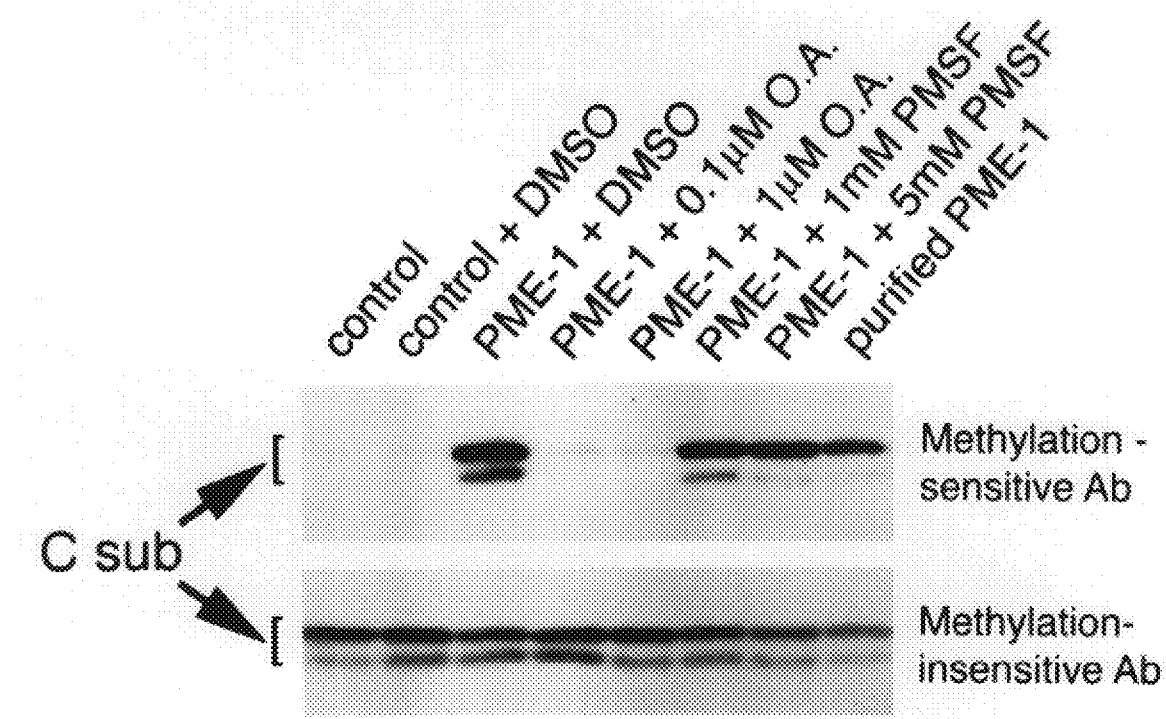
FIG. 5 shows that human PME-1 is a PP2A methylesterase. Immunoprecipitated PP2A C subunit was incubated with lysates from bacteria either not expressing PME-1 (control) or expressing PME-1 (PME-1), or with purified bacterially-expressed PME-1 (~5 ng). Okadaic acid (O.A.) or PMSF was added to the reactions to the indicated final concentrations. Reactions containing 1.25% DMSO as a control to match the level resulting from addition of okadaic acid or PMSF stock solutions is noted. After incubation, the immunoprecipitated PP2A C subunits were analyzed by SDS-PAGE. Proteins were transferred to nitrocellulose and the membrane was probed with 4b7 (methylation-sensitive Ab), an anti-C subunit antibody that only recognizes unmethylated C subunits. Subsequently, the same membrane was probed with Transduction Laboratories, (Lexington, Ky.) anti-PP2A C subunit antibody (methylation-insensitive Ab), which is insensitive to the methylation state of PP2A and therefore reveals the total C subunit in each lane. The C subunits migrated as doublets in this gel, but whether double or single bands are seen can vary (see comments in legend to FIG. 2A).

A PP2A C subunit carboxyl methylesterase of 46 kDa has recently been purified [Lee, J. et al., (1996) Proc. Natl. Acad. Sci., USA 93:6043–6047] but no sequence information was reported. To test the possibility that PME-1 might be a PP2A methylesterase, PME-1 was expressed in bacteria and bacterial lysates were tested for methylesterase activity towards PP2A C subunit as described in the Examples herein. The results shown in FIG. 5 demonstrate that lysates of bacteria expressing PME-1 contain a PP2A methylesterase activity not found in bacterial lysates lacking PME-1. Similar results were obtained with purified recombinant PME-1 (FIG. 5). These results indicate that PME-1 is indeed a PP2A methylesterase. Because its specificity towards other methylated phosphatases (such as PPX) has not been characterized, it was generically named Protein Phosphatase Methylesterase-1 (PME-1).

The 46 kDa PP2A methylesterase reported by Lee and coworkers was inhibited by okadaic acid, a potent PP2A inhibitor, but not by PMSF, a covalent inhibitor of certain serine esterases. To determine if PME-1 displays similar sensitivities to these inhibitors, the above demethylation assay was also conducted in the presence of okadaic acid and PMSF (FIG. 5). The methylesterase activity of bacterially expressed PME-1 was inhibited by 0.1 or 1 μM okadaic acid but not by 1 or 5 mM PMSF, similar to the methylesterase purified by Lee et al. (1996) supra.

Figure 6A:
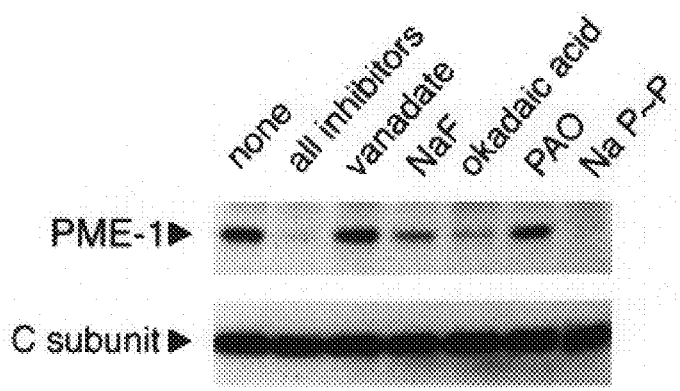
FIG. 6A shows that the PP2A inhibitors, okadaic acid, sodium fluoride, and sodium pyrophosphate, reduce the amount of PME-1 complexed with the catalytically inactive H59Q C subunit. Seven parallel dishes of NIH3T3 cells expressing HA-tagged H59Q were lysed in NP40 lysis buffer containing the indicated inhibitor(s) at the following concentrations: sodium vanadate (1 mM); NaF (50 mM); okadaic acid (500 nM); phenylarsineoxide (PAO; 10 $\mu$M); sodium pyrophosphate ($Na_4P_2O_7$; 20 mM). Anti-HA tag immunoprecipitates were prepared from these lysates and analyzed by SDS-PAGE and immunoblotting. The blot was probed sequentially with antibodies detecting PME-1 and H59Q C subunit (via its HA tag). In a separate experiment using phosphorylase a as substrate, sodium fluoride, okadaic acid and sodium pyrophosphate were respectively found to inhibit PP2A 91±10%, 97±4%, and >99%, while phenylarsineoxide and sodium vanadate respectively showed no or 25±18% inhibition.

Because single amino acid changes in the C subunit active site were capable of inducing stable complex formation of C subunit with PME-1, it was of interest to determine if PP2A inhibitors could antagonize the H59Q/PME-1 complex. To assay for this possibility, NIH3T3 cells expressing epitope-tagged H59Q C subunit were lysed in the presence of various phosphatase inhibitors and H59Q was immunoprecipitated via its epitope tag. The amount of endogenous, untagged PME-1 coimmunoprecipitating in each case was assayed by blotting with anti-PME-1 antibody (FIG. 6A). Inhibitors to which PP2A is highly sensitive (okadaic acid, sodium fluoride, and sodium pyrophosphate), but not those to which PP2A is less sensitive or insensitive (vanadate and phenylarsineoxide, respectively), decreased the amount of PME-1 bound to H59Q.

Figure 6B:
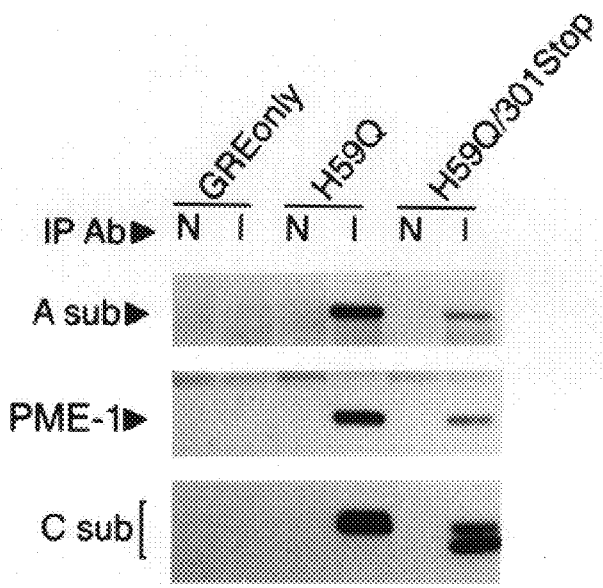
FIG. 6B shows that loss of the C subunit carboxy-terminus reduces, but does not abolish, PME-1 Binding. Non-immune (N) and HA tag (I) immunoprecipitates were prepared from MT-transformed NIH3T3 cells expressing vector only (GRE only), HA-tagged H59Q, or HA-tagged H59Q/301Stop double mutant which lacks nine carboxy-terminal amino acids. Immune complexes were analyzed by SDS-PAGE; proteins were transferred to nitrocellulose; and immunoblotting was performed with antibodies directed against A subunit, PME-1, and C subunit (anti-HA tag). The C subunits migrate as doublets in this gel, but whether double or single bands are seen can vary (see comments in legend to FIG. 2A). The band seen in all lanes in the PME-1 panel is from the immunoprecipitating antibodies. Chemiluminescent quantitation (using a Biorad Fluor-S Max Multiumager, Hercules, Calif.) was used in seven separate experiments with mixtures of clones to quantify the ratio of PME-1 to C subunit signal in each lane. In six of seven experiments with mixes of clones, the double mutant bound less PME-1 than did H59Q, with a mean reduction of 56±30% and a median value of 39 (range of 8–87%). Thus, PME-1 binding is clearly reduced by loss of the carboxy-terminus. In a seventh experiment, for unknown reasons, the double mutant bound 235 % of the H59Q level of PME-1, lowering the overall mean reduction to 28% (median=40).

A PP2A methylesterase might be expected to make important contacts with carboxy-terminal residues. However, Lee and coworkers found that PP2A carboxy-terminal peptides functioned neither as inhibitors nor as substrates for their 46 kDa PP2A methylesterase, suggesting that, at a minimum, contacts with other parts of the C subunit are essential. To investigate the importance of the H59Q C subunit carboxy-terminus for stable interaction with PME-1, a double mutant, H59Q/301Stop, was created. This mutant combines the H59Q mutation, which induces stable binding of PME-1, with a deletion of the nine C subunit carboxy-terminal acids, 301–309. FIG. 6B shows the results of an immunoprecipitation assay measuring the relative abilities of H59Q and H59Q/301Stop to bind A subunit and PME-1. Deletion of residues 301–309 from wt C subunit has previously been found to decrease the amount of A subunit bound [Ogris, E. et al. (1997) supra]. FIG. 6B shows that deletion of these residues from H59Q also reduces the binding of the PP2A A subunit to H59Q. In addition, although similar amounts of H59Q and H59Q/301Stop were immunoprecipitated in this experiment, the double mutant bound less PME-1 than did H59Q, indicating that one or more of the deleted carboxy-terminal residues is important for H59Q/PME-1 complex formation. PME-1 binding was not completely abolished, however, demonstrating that interactions also exist between PME-1 and other residues in the C subunit.

Figure 6C:
FIG. 6C demonstrates that subunit carboxy-terminal antibodies immunoprecipitate reduced amounts of H59Q/PME-1 Complex. Immunoprecipitates were prepared from MT-transformed NIH3T3 cells expressing HA-tagged H59Q using control antibody, HA-tag antibody (12CA5), or carboxy-terminal C subunit antibodies (1D6, 4B7, 4E1). The immune complexes were analyzed by SDS-PAGE; proteins were transferred to nitrocellulose; and immunoblotting was performed with anti-A subunit antibody (upper panel), anti-PME-1 antibody (middle panel) and anti-C subunit antibody recognizing both endogenous and HA tagged proteins (1D6; lower panel). The positions of A subunit, the immunoprecipitating antibody heavy chains (Ab), PME-1, HA-tagged H59Q C subunit, and untagged, endogenous wt C subunit are indicated. The C subunits migrate as single bands in this gel, but whether double or single bands are seen can vary (see comments in legend to FIG. 2A). HA-tagged H59Q C subunit migrates more slowly than endogenous wt C subunit because of the HA tag.

To address the same question via a different approach, we assayed via immunoprecipitation whether antibodies directed against the C subunit carboxy-terminus would compete with PME-1 for binding to H59Q. If an antibody competes with PME-1 for binding to residues on H59Q that are important for PME-1 association, that antibody would be expected to coimmunoprecipitate reduced amounts of PME-1 with H59Q when compared to an antibody that does not compete with PME-1. The carboxy-terminal C subunit monoclonal antibodies used for this experiment, 1D6, 4B7, and 4E1, were recently generated against a 15-residue unmethylated carboxy-terminal peptide. These antibodies are unable to efficiently recognize a C subunit mutant lacking the carboxy-terminal leucine, indicating that they bind, at least in part, at the very carboxy-terminus. A positive control monoclonal antibody, 12CA5, immunoprecipitates H59Q via its amino-terminal epitope tag and should not interfere with interactions at the C subunit carboxy-terminus [Ogris, E. et al. (1997) supra]. Comparison of the relative ratios of the PME-1 and H59Q bands in FIG. 6C reveals that, relative to 12CA5, 1D6 and 4B7 inimunoprecipitate less PME-1 for the same amount of H59Q C subunit (the band of endogenous, wt C subunit immunoprecipitated by the carboxy-terminal antibodies can be ignored as wt C subunit does not associate stably with PME-1). Furthermore, although 4E1 immunoprecipitated a substantial amount of H59Q C subunit (within approximately two-fold of 12CA5), no PME-1 could be detected even on long exposures. These results thus further substantiate the conclusions made from FIG. 6B. In addition, the fact that 1D6 and 4B7 coimmunoprecipitate similar amounts of PME-1, but dramatically different amounts of A subunit indicates that PME-1 binding does not appear to be dependent on A subunit binding.

The successful identification of the first of a number of cellular proteins that stably associate with catalytically inactive PP2A C subunit mutants, but not with wt C subunit, is reported herein. Two proteins of 44 kDa that differ in their isoelectric points, PME-1 and p44B, uniquely associated with two different catalytically inactive C subunit mutants substituted individually at two different active site histidine residues. PME-1 was affinity purified and a cDNA encoding it was cloned. This protein was identified as a PP2A methylesterase by several criteria including 1) molecular size; 2) the presence of a motif found in lipases that use serine as their nucleophilic catalytic residue; 3) activity assays performed in vitro with bacterially expressed protein; and 4) the ability of okadaic acid, a known inhibitor of both PP2A and the PP2A methylesterase, to inhibit its activity and decrease its association with the catalytically inactive C subunit mutant, H59Q.

Based on its molecular size, sensitivity to okadaic acid, and the lack of effect of PMSF on PME-1 activity, PME-1 is likely to be equivalent to the 46 kDa PP2A methylesterase whose purification and initial characterization was recently reported by Lee and colleagues [Lee, J. et al. (1996) supra]. Its insensitivity to PMSF indicates that it is not the PMSF-sensitive serine esterase/protease activity reported by Xie and Clarke [Xie, H. et al. (1994) *Biochem. Biophys. Res. Commun.* 203:1710–1715], which also could remove PP2A carboxymethyl groups. Lee and coworkers (1993 supra) reported that their purified PP2A methylesterase eluted as two different peaks from an anion exchange column, consistent with either differential modification or the existence of two closely related isoforms of the enzyme. The amounts of these two species were within several fold of each other. Two pieces of evidence from our studies support the idea that those two forms probably represent differentially modified forms of the enzyme. First, probing of the GenBank EST database with the PME-1 cDNA sequence provides no evidence for a closely related PME-1 isoform, even though numerous ESTs are found which correspond precisely to the PME-1 cDNA sequence. Second, Northern blot analysis yielded a single band in multiple organs. In addition, we have found via immunoblotting that mammalian PME-1 in cell lysates migrates on two-dimensional gels as two spots differing in their isoelectric point in a manner consistent with a single charge difference.

The molecular basis of the cell cycle-dependent regulation of PP2A C subunit methylation is unknown. The poor metabolic labeling of PME-1 in an asynchronous population of cells relative to a number of other proteins suggests that this protein is quite stable. This result argues against the possibility that cell cycle PP2A methylation is regulated by modulating the amount of the PP2A methylesterase. Whether PME-1 activity is regulated is unknown. In the case of the bacterial chemotactic response, the CheB methylesterase is regulated by phosphorylation [Wylie, D. et al. (1998) *Biochem. Biophys. Res. Commun.* 151:891–896; Hess, J. F. et al. (1998) *Cell* 53:79–87] while the methyltransferase is thought to be constitutively active. Lee and coworkers (1996 supra) found no difference in the activity of their two purified forms of PP2A methylesterase, suggesting that the differential modification likely responsible for generating these two forms might not be involved in regulation of activity of this enzyme. It is possible, however, that effects might be seen under other conditions, or that an additional protein(s) may be necessary for an effect to be manifested. In addition, it is possible that more than one modification occurs.

Without wishing to be bound by any particular theory, it is believed that PP2A methyltransferase and methylesterase enzymes achieve their specificity, in part, by interacting with or near the active site of the PP2A C subunit. It was reported previously that neither the PP2A methyltransferase nor the PP2A methylesterase can recognize short peptide substrates corresponding to the C subunit carboxy-terminus. Thus, functional recognition by both these enzymes requires additional C subunit structure. Additionally, as demonstrated in this study, perturbation of the C subunit active site by either of two different mutations can stabilize the interaction with the PME-1 methylesterase. Furthermore, PP2A inhibitors have a destabilizing effect on the PME-1/H59Q interaction. Finally, the methyltransferase is inhibited by the PP2A inhibitors, okadaic acid and microcystin-LR, and the methylesterase is inhibited by okadaic acid (testing for inhibition of the methylesterase by microcystin has not been reported). Although it has been proposed that this inhibition is due to the interaction of these inhibitors with carboxy-terminal C subunit residues, the PP2A inhibitors, sodium fluoride or sodium pyrophosphate, partially or fully disrupt PME-1/H59Q complexes. The latter effect is more consistent with a role in binding the PME-1 methylesterase for active site residues and/or metals, or nearby residues sensitive to effects on the active site. Four separate catalytically inactive PP2A active site point mutants including the two described in this study, are methylated at less than 3% of the wild-type level in vivo and in vitro. Although we believe there is interaction with residues and/or metals in or near the active site, but another equally viable possibility is that mutation of active site residues and/or binding of inhibitors has more distant effects on the C subunit conformation critical for stable complex formation with PME-1.

Contact between the C subunit and PME-1 could be with PME-1 residues and/or with a phosphorylation site on PME-1. Because H59Q and H118Q are virtually unmethylated, PME-1 apparently can remain bound to these mutants in the absence of a methylated carboxy-terminus. At least with H59Q, PME-1's contacts other than on the C subunit carboxy-terminus are strong enough to result in substantial complex formation in the absence of the nine carboxy-terminal C subunit residues. This conclusion is further supported by the finding that two C subunit carboxy-terminal peptide antibodies, known to require Leu 309 for efficient binding, immunoprecipitate H59Q/PME-1 complexes. However, the amount of PME-1 coimmunoprecipitated by these antibodies was less than that coimmunoprecipitated by an antibody recognizing an amino-terminal epitope tag on the C subunit. The latter result and the fact that a third carboxy-terminal C subunit antibody could not imrnunoprecipitate H59Q/PME-1 complexes at all suggest that PME-1 is proximal to the C subunit carboxy-terminus in the H59Q/PME-1 complex. Moreover, the reduced amounts of PME-1 in complex with the H59Q/301Stop double mutant indicate that carboxy-terminal residues play a role in binding of H59Q to PME-1. The contribution of these residues to the interaction of wild type C subunit with PME-1 might be even more important in the absence of the complex-stabilizing H59Q mutation.

The decreased B subunit binding observed with these mutants might be due indirectly to lack of methylation at the carboxy-terminus of these mutants. The fact that H59Q and H118Q bind the structural PP2A A subunit and polyomavirus MT suggests that they are not grossly altered in their structure. Two other catalytically inactive point mutants that bind A subunit and polyomavirus MT, but are highly deficient in methylation are also deficient in B subunit binding. Given that the B subunit requires the C subunit carboxy-terminus for stable complex formation with the A/C heterodimer, the B subunit might require a methylated carboxy-terminus for efficient binding to C subunit. An alternate, but not mutually exclusive, possibility is that the carboxy-terminus and the active site are proximal in the three dimensional structure of the C subunit. This model would provide an explanation for how events occurring at the carboxy-terminus (B subunit binding, methylation, phosphorylation, etc.) can affect the active site (activity, specificity), and vice versa. In addition, at least for H59Q and H118Q, PME-1 and B subunit binding might be mutually exclusive.

These catalytically inactive C subunit mutants should be useful for identifying other proteins involved in PP2A signaling. H59Q and H118Q bind multiple proteins not bound stably by wt C subunit. These include, in addition to PME-1, p44B and other proteins not marked, but visible, in FIG. 2B. Interestingly, initial experiments suggest that p44B binding to H59Q is even more sensitive to phosphatase inhibitors than is PME-1 binding. These proteins could be PP2A substrates or other proteins whose binding is sensitive to the state of the C subunit active site. One of these proteins is the same molecular size as the PP2A methyltransferase reported by Lee and colleagues (Lee et al. (1993) supra]. Catalytically inactive mutants of dual specificity and tyrosine phosphatases [Gelerloos, J. A., et al. (1996) Oncogene 13:2367–2368; Bliska, J. B. et al. (1992) J. Exp. Med. 176:1625–1630] have been previously used successfully to identify novel substrates, but unlike PP2A, their catalytic mechanisms involve the formation of covalent intermediates with substrates.

PME-1 and p44B differ in several characteristics, suggesting that these two proteins are not simply modified forms of one another. They are separated from each other on two-dimensional gels by approximately one pH unit, which is unlikely to be accounted for by modification; PME-1 forms sharp spots on these gels while p44B migrates as a smear. In addition, in vitro translation of PME-1 yields no product migrating at the position of p44B and we have been unable to detect p44B with antibodies raised against PME-1 sequences.

Finally, because of the high conservation of PP2A with other phosphatases such as PP1, PPX, PPV, etc., it will be of interest to see if similar or different cellular proteins bind stably to these phosphatases when the residues corresponding to PP2A H59 and H118 are mutated to glutamine. One question of special interest is whether the corresponding catalytically inactive mutants of PPX, which has the same last four carboxy-terminal amino acids as PP2A and is also methylated at its carboxy-terminal leucine, will also trap PME-1.

The present invention provides the coding sequences for the mammalian PME1 protein, as specifically exemplified by the human coding sequence. This allows the construction of recombinant DNA molecules and recombinant host cells produced in the laboratory, which molecules and host cells are used for the recombinant expression of the PME1 protein and enables assay methods for determining inhibitors of the methylesterase activity of the PME-1 protein, and thus, compounds which slow the growth of cells, especially neoplastic and/or transformed cells.

Without wishing to be bound by theory, the present inventors propose that the protein of the present invention is a Protein Phosphatase Methylesterase-1 (PME-1) which removes methyl groups from the PP2A growth-regulating protein phosphatase, and that the methylation status of the catalytic subunit affects activity and thus plays a role in growth regulation and normal progression of the cell cycle. See, e.g., Lee et al. (1996) supra, for a description of the methylesterase and methods for assay.

Monoclonal or polyclonal antibodies, preferably monoclonal, specifically reacting with the methylesterase of the present invention encoded by a particular coding sequence may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) supra; Maniatis et al. (1982) *Molecular Cloning*, Cold Spring Harbor Laboratory, Plainview, N.Y.; Wu (ed.) (1993) *Meth. Enzymol.* 218: Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) DNA Cloning Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

All references cited in the present application are incorporated by reference herein to the extent that they are not inconsistent with the present Specification.

The following examples are provided for illustrative purposes, and are not intended to limit the scope of the invention as claimed herein. Any variations in the exemplified sequences and methods which occur to the skilled artisan are intended to fall within the scope of the present invention.

EXAMPLES

Example 1

Plasmids and Mutagenesis

Site-directed mutagenesis was performed on a HA-tagged wt C subunit cDNA cloned in the pcDNA I Amp vector [Ogris et al. (1997) supra] using the Muta-Gene Phagemid In Vitro Mutagenesis Kit according to the manufacturer's instructions (Bio-Rad Laboratories, Hercules, Calif.). The entire cDNA of both H59Q and H118Q was sequenced to confirm successful mutagenesis and to ensure that no additional mutation occurred. Mutant C subunit cDNAs including the HA tag coding sequence were cloned into the dexamethasone-inducible vector, pGRE 5-2 [Mader, S., and White, J. H. (1993) Proc. Natl. Acad. Sci. USA 90:5603–5607]. The construction of a pGRE5-2 vector expressing HA-tagged wt PP2A C subunit has been previously described [Ogris et al. (1997) supra]. An inducible vector was chosen to try to minimize the potential deleterious effects of wild-type and mutant C subunits (if any) while lines were being carried in culture, and to provide for an uninduced control in analyses of their effects.

Example 2

Cells and Cell Culture

NIH 3T3 lines expressing wt polyomavirus MT and a geneticin resistance gene [Cherington et al. (1986) Proc. Natl. Acad. Sci. USA 83:4307–4311] were transfected by the calcium phosphate precipitation method [Sambrook et al. (1989) supra], and individual clones and mixtures of clones expressing wt C subunit (36 wt), H59Q, H118Q, or empty vector (GREonly) were selected and maintained as described previously [Ogris et al. (1997) supra]. H118Q expressed at a level well below that of endogenous wt C subunit, while H59Q expressed at a level equal to or greater than the wt level. Although the inducible vector, pGRE5-2, was used to express these proteins, their levels were substantial in the absence of dexamethasone; for this reason, GREonly cells were used as a negative control in this study rather than uninduced wt or mutant C subunit expressing cells. However, dexamethasone treatment was always used to obtain maximal expression of the C subunits.

Example 3

Radiolabeling of Cells

For metabolic labeling of cells with methionine, subconfluent dishes of cells were labeled for 5 h with [$^{35}$S] methionine (300 uCi/ml) in DMEM minus methionine supplemented with 0.5% dialyzed fetal bovine serum.

Example 4

Preparation of Cell Lysates and Immunopreciptation

The details of treating the cells with dexamethasone, preparation of cell lysates, and immunoprecipation of C subunits have been described previously [Ogris et al. (1997) supra]. For experiments quantitating PME-1 binding to different mutants (FIG. 6B), immunoprecipates were washed twice with NP40 lysis buffer, twice with PBS, and once with ddH20. Washed immune complexes were used for phosphatase assays or analyzed by one or two-dimensional gel electrophoresis.

Example 5

One- and Two-dimension I Gel Electrophoresis and Fluorography

SDS-polyacrylamide gel (10% acrylamide) was performed according to Laemmli [Laemmli, U.K. (1970) Nature 227:680–685]. Gels were silver stained by the procedure of Wray et al. [Wray, W. et al. (1981) Biochemistry 118:197–203] except that after electrophoresis the gels were sequentially incubated 10 min in distilled water (200 ml), 10 min in 95% ethanol (200 ml), 1 h. in 50% methanol (100 ml), and 30 min in distilled water (100 ml) prior to staining.

Example 6

Immunoblotting

Immunoblotting [Towbin, H. et al. (1979) Proc. Natl. Acad. Sci. USA 76:4350–4354] was performed with mouse monoclonal anti-tag antibody (16B12; 1:5000 dilution of ascites; BAbCO, Richmond, Calif.); rabbit anti-B subunit antibody (#16; 1:5000); affmity-purified rabbit (R39; 1:5000) or mouse monoclonal (4G7; 1 μg/ml) anti-A subunit antibodies; mouse monoclonal anti-C subunit antibody (1D6; 0.25 μg/ml); or rabbit ant-PME-1 antibodies (AR2 or E37; see below). Immunoblots were developed with enhanced chemiluminescences (Amersham, Arlington Heights, Ill.).

Example 7

Phosphatase Assay

Phosphatase activity present in anti-HA tag immunoprecipitates from the different cell lines was assayed using phosphorylase a and Histone H1. [γ-$^{32}$P]-labeled phosphorylase a substrate was prepared from phosphorylase b according to the manufacturer's (GibcoBRL, Gaithersburg, Md.) instructions. Histone H1 was phosphorylated by mitotic p34$^{cdc2}$ purified from Nocodazole arrested HeLa cells as described [Mayer-Jaekel et al. (1994) supra]. Lysates used for immunoprecipitation were equilibrated according to epitope-tagged C subunit expression levels. Assays were performed at a linear range and with subsaturating amounts of each substrate.

Example 8

Purification and Microsequencing of PME-1

To obtain PME-1 protein for microsequencing, H59Q C subunit complexes containing PME-1 were immunoaffmity purified. In total, 135 confluent 15 cm dishes of MT-transformed NIH3T3 cells expressing HA-tagged H59Q were needed to obtain enough PME-1 for microsequencing. Forty-five separate inmunoaffinity purifications were performed on 3 dishes of lysate at a time, reusing the same immunoaffinity matrix at least 15 times. To prepare the immunoaffinity matrix, anti-HA tag antibody (12CA5; obtained from BAbCO) was chemically crosslinked to protein A-Sepharose beads (Pharmacia, Piscataway, N.J.) by published methods [Harlow, E., and Lane, D. (1988) supra]. After washing 3 dishes of cells twice with PBS and once with IP wash (10% (vol/vol) glycerol; 135 mM NaCl; 20 mM Tris, pH 8.0), the cells were scraped and lysed at 4° C. with rocking for 10 min in 1.0 ml of NP40 lysis buffer (IP wash containing 1% Nonidet P-40, 1 mM phenylmethylsulfonyl fluoride, and 0.03 units/ml aprotinin). Lysates were cleared at 13,000×g, and then incubated for 1 h at 4° C. while rocking with 500 µl of the crosslinked antibody/bead complexes. Complexes were washed once with NP40 lysis buffer, three times with Tris-buffered saline, and then twice with ddH$_2$O. Bound H59Q complexes containing PME-1 were eluted by three sequential incubations with 300 µl of 20 mM triethylamine. Eluates were quickly frozen on dry ice and stored frozen until all batches of affinity purification had been completed. The antibody/bead complexes were then washed twice with 20 mM triethylamine and twice with IPlyse prior to reuse. After H59Q complexes had been purified from all 135 dishes of cells, eluates containing PME-1 were concentrated to dryness by vacuum centrifugation, and the residues were suspended in PBS and gel buffer and analyzed on three separate SDS-polyacrylamide gels [Laemnmli, U.K. (1970) *Nature* 227:680–685]. One-dimensional gels were chosen to avoid losses associated with 2D gel analysis. Because PME-1 migrates closely to actin, the separation of these two proteins was maximized by the use of an 8% SDS-polyacrylamide gel run for an extended period of time.

Example 9

Trypsin digestion, HPLC separation and microsequencing

After separation of PME-1 complexes by SDS-PAGE, the proteins were electrotransferred to polyvinylidiene difluoride (PVDF) membrane and stained with Ponceau S. Individual protein bands were excised and submitted to in situ digestion with trypsin [Fernandez et al. (1994) *Anal. Biochem.* 218:112–117; Lane et al. (1991) *J. Protein Chem.* 10:151–160]. The resulting peptide mixture was separated by microbore high performance liquid chromatography using a Zorbax C18 2.1 mm by 150 mm reverse phase column on a Hewlett-Packard 1090 HPLC/1040 diode array detector. Optimum fractions from the chromatogram were chosen based on differential UV absorbance at 205 nm, 277 nm and 292 nm, peak symmetry and resolution. Peaks were further screened for length and homogeneity by matrix-assisted laser desorption time-of-flight mass spectrometry (MALDI-MS) on a Finnigan Lasermat 2000 (Hemel, England); and selected fractions were submitted to automated Edman degradation on an Applied Biosystems 494A, 477A (Foster City, Calif.) or Hewlett Packard G1005A (Palo Alto, Calif.). Details of general strategies for the selection of peptide fractions and their microsequencing have been previously described [Lane et al. (1991) supra].

Example 10 cDNA Cloning via PCR and RT-PCR

To obtain the missing 5' portion of the PME-1 coding region, nested and seminested PCR were performed using human B cell, human hippocampus, and human kidney cDNA plasmid libraries. 5' primers corresponded to vector sequence that flanked cDNA inserts in the library being used as template, while 3' primers corresponded to known sequence (EST or newly derived 5' PME-1 sequence). Southern Blotting using an end-labeled 20 bp oligonucleotide corresponding to known PME-1 sequence upstream of the 3' PCR primer was employed to identify authentic PME-1 products after each reaction. PCR products containing 5' extensions of the PME-1 sequence were purified using a PCR product purification kit (Boehringer-Mannheim, Indianapolis, Ind.), cloned, and sequenced. New primers were designed for PCR and Southern Blotting and then the above steps were repeated until the sequence of the remainder of the PME-1 coding region and a portion of the 5' UTR were obtained.

Total mRNA was purified from HeLa cells using Trizol Reagent (Life Technologies, Gaithersburg, Md.) according to the manufacturer's instructions. RT-PCR was employed to obtain a PME-1 cDNA from HeLa cell mRNA. First strand synthesis was performed with Avian Myeloblastosis Virus reverse transcriptase (Boehringer-Mannheim, Indianapolis, Ind.) by the manufacturer's protocol using a primer from the PME-1 3' UTR (TGTTGAGGAGGGGTGGACAG) (SEQ ID NO: 1). Using pfu polymerase (Stratagene, La Jolla, Calif.), the product was used for PCR with the same 3' primer and a primer from the PME-1 5' UTR (TGTATGGGGACCTTCCTCCT) (SEQ ID NO:2) to generate a cDNA containing the entire PME-1 coding region and much of the 5' UTR, including the in frame stop codon upstream of the putative start ATG.

Obtaining the entire human PME-1 coding sequence required hundreds of PCR reactions, scores of oligonucleotide primers, many Southern blots and numerous subclonings and sequencing reactions. Most libraries did not contain cDNAs with a full length PME-1 coding sequence.

Example 11

Purification of His-tagged PME-1 from bacteria expressing recombinant His-tagged PME-1

*E. coli* (PR13Q) expressing recombinant His-tagged PME-1 from an isopropylthiogalactoside (IPTG) inducible lac promoter were grown to an O.D. at 600 nm of 0.7 and then induced with IPTG for 2–3 h. The PME-1 coding sequence is fused in frame in a vector such as pThioHis A, B, C, pTrcHis A, B, C or pTrcHis 2A, B, C (Invitrogen, Carlsbad, Calif.). Cells were collected by centrifugation and broken open in the presence of protease inhibitor by sonication or use of a French Pressure cell, using a lysis buffer containing normal saline (137 mM), and 20 mM TrisHCl (pH8.0). Lysates were cleared by centrifugation at $\geq$13,000×g, and supernatants were incubated in batch with a nickel-agarose column matrix (Chelating Sepharose, Pharmacia, Piscataway, N.J.) for 1–2 h at 4° C. with rocking. Alternatively, a packed nickel-agarose column was used and the supernatant was passed over it slowly several times. In either case the nickel-agarose/6XHis-PME-1 complexes were washed and then His-tagged PME-1 was eluted with increasing amounts of imidizole (either with a step or continuous gradient). PME-1 protein thus isolated was dialyzed to remove the imidizole or analyzed on a Mono-Q column. Milligram amounts of PME-1 protein have been obtained from a liter of culture.

Example 12

Assay for PP2A methylesterase activity

Epitope-tagged PP2A C subunits with $^3$H-methyl groups incorporated in vitro were immunoprecipitated with anti-tag antibody and used as substrate for PME-1. PME-1 enzyme sources assayed include: lysates of bacteria or baculovirus-infected Sf9 insect cells expressing His-tagged PME-1 and immunoprecipitated PME-1 from baculovirus-infected Sf9 insect cells. Control lysates from bacteria or Sf9 cells not expressing recombinant PME-1 were also incubated with tritiated substrate to measure non-specific background from the lysates. After 1 h incubation at 32° C., the amount of $^3$H-methyl groups remaining was assayed by SDS-polyacrylamide gel electrophoresis (SDS-PAGE). PME-1 was clearly able to demethylate PP2A C subunit as measured by this assay. The HA-tagged PME-1 expressed in the baculovirus vector has been demonstrated to have PP2A methylesterase activity.

In a second methylesterase assay, unlabeled epitope-tagged PP2A C subunits were immunoprecipitated with anti-tag antibody and used as substrate for PME-1. As PME-1 enzyme source, the following were used: cell lysates of bacteria expressing HA-tagged, His-tagged, and untagged PME-1; cell lysates of HA-tagged or untagged PME-1-expressing baculovirus-infected Sf9 insect cells; purified bacterial HA-tagged PME-1, purified (immunoprecipitated) baculovirus-infected Sf9 HA-tagged PME-1. Control lysates from bacteria or Sf9 cells not expressing recombinant PME-1 were also incubated with substrate to measure non-specific background from the lysates. After 1 h incubation at 32° C., the C subunit immunoprecipitates were washed and analyzed by SDS-PAGE. The proteins in the gels were electrophoretically transferred to nitrocellulose membranes and then the membranes were probed with monoclonal antibody (made in our laboratory) that only recognizes unmethylated PP2A. A second probing of the same membrane with a methylation-insensitive antibody shows the actual amount of PP2A C subunit in each lane. Comparison of the blotting signals for the two different antibodies allow demethylation to be evaluated (the signal of the methylation-inhibited antibody gets stronger as PP2A C subunit is demethylated). PME-1 was clearly able to demethylate PP2A C subunit, as measured by this assay.

An in vitro methylesterase activity assay using the PME-1 protein, for example, produced as a recombinant human PME-1, can be used to screen test compounds for inhibition of PME-1. Inhibitors of PME-1 in e.g., neoplastic cells slow the growth of those cells. Inhibitors could also be used to slow the growth in other hyperproliferative conditions. In Alzheimer's disease, PP2A has reduced activity. Identification of compounds which increase PP2A activity, for example, by appropriately modulating PME-1 activity, allows treatment to slow the progression of Alzheimer's disease, and thus postpone loss of mental function in affected patients.

Example 13

Computer analyses

The NCBI BLAST program [Altschul, S. F. et al. (1990) J. Mol. Biol. 215:403–410] was used to probe various databases for PME-1 ESTs and related proteins. The DNAS-TAR Lasergene software package was utilized for alignments and identification of the PROSITE database lipase motif found in PME-1.

Example 14

Northern Blot

Adult Balb/c mice were sacrificed and organs removed and flash-frozen in liquid nitrogen. total RNA from the organs was isolated using the RNeasy kit (QIAGEN), and analyzed on formaldehyde-1% agarose gels to check for RNA integrity and to estimate the amount of the 18S and 28S RNAs. Based on these estimates, similar amounts of RNA were separated on formaldehyde-1% agarose gels and transferred to GeneScreen nylon membranes. After UV-crosslinking, the membranes were stained with a 0.04% methylene blue solution to visualize the RNA. Filters were then hybridized with a $^{32}$P-radiolabeled probe generated by random primer labeling of a DNA fragment from the 3' untranslated region of the mouse PME-1 cDNA. the probe, 395 bp in length, is an EcoRI-NotI fragment of a PME-1 EST clone (accession number W34856). The blots were used for autoradiography with X-ray film and/or analyzed on a STORM Phosphorimager (Molecular Dynamics, Sunnyvale, Calif.).

Example 15

Production of Polyclonal Antibodies Recognizing PME-1

Two different antisera recognizing PME-1 were raised in rabbits. The first AR2, was raised against a 16-residue PME-1 peptide sequence (RIELAKTEKYWDGWFR) (amino acids 288–303, SEQ ID NO:5) found encoded in the PME-1 cDNA. The peptide was conjugated to Keyhole Limpet Hemocyanin (KLH) via an added carboxy-terminal cysteine residue using a Piece Imject conjugation kit, and the conjugate was used as immunogen. The second antiserum, E37, was raised against a mixture of two-nickel agarose-purified, 6xHis-tagged, bacterially expressed human PME-1 fragments that together represent the carboxy-terminal half of the protein. For each immunogen, a single female New Zealand white rabbit was immunized and boosted multiple times using Freund's adjuvant.

Example 16

PME-1 Sequences from other organisms

Yeast PME-1 was found by homology searches of sequence databases using the NCBI BLAST program and the known human PME-1 sequence. Genomic yeast PME-1 sequence was examined and found to have no introns; therefore, we designed PCR primers for yeast PME-1 carried out PCR, cloned the PCR product into a bacterial vector and sequenced it to make sure no PCR errors had occurred.

Table 3 shows the amino acid sequence of the yeast methylesterase homolog of PME-1. Table 6 provides the coding sequence for the yeast PME-1 protein.

The C. elegans PME-1 coding sequence was deduced by homology with mammalian and yeast PME-1 sequenced. However, it should be noted that this gene product was not predicted by the Genefinder program.

Table 4 provides the amino acid sequence of the C. elegans PME-1 homolog and Table 7 gives the coding sequence. Review of the EST sequences revealed two potential alternative splicing scenarios. The alternate which encoded an LLSTYCR amino acid segment (SEQ ID NO: 17) was ruled out based on the lack of a similar amino acid segment in the yeast PME-1 protein and poor alignment with the human protein sequence.

Table 9 illustrates the alignment of human, C. elegans and S. cerevisiae (YHN5) PME-1 protein sequences. Residues identical with human PME-1 are as white-on-black. Residues corresponding to the Prosite motif for lipases employing an active site serine are boxed.

The mouse PME-1 sequences were found by search for EST sequences on GenBank with significant homology to the human PME-1 DNA sequences disclosed herein. Table 5 represents a portion of the mouse coding sequence generated by homology searches and computer-aided alignment of the mouse sequences to the human sequences and creating a consensus sequence for the nucleotides of the various homologous ESTs. The first 283 nucleotides of Table 5 are from a single EST (GenBank Accession No. AA555778). The next 465 nucleotides are given as X's because there was no mouse sequence homologous to the corresponding human PME-1 cDNA sequence. It is understood that the actual length may not be exactly 465 nucleotides. The following 527 nucleotides are from a single mouse EST (Accession No. AA644991.) The next seven nucleotides (1276–1282) are from an overlap of AA644991 with AA672810. The following 132 nucleotides are from AA 672810 only. Then two other ESTs overlap; thus, most of the remaining nucleotides are quite certain, with the following exceptions. The nucleotides at positions 1942–1943 at somewhat ambiguous in that two ESTs have the identified sequence while others have TA, TN or T-. The G at position 2167 is from 2 of 3 ESTs. R at 2169 is from a G and A in two ESTs. The sequence at 2174–2175 appears unreliable. Nucleotides 2247–2270 are from a single EST (Accession No. EST AA260585) and nucleotides 2337–2409 are from a single minus-strand EST (Accession No. T25552).

Plants also have similar growth regulatory phosphatase-kinase-methylation-demethylation systems, and there is a plant protein having significant homology to the mouse, human, yeast and nematode (*C. elegans*) PME-1 sequences, especially to the catalytic and GQMQGK (amino acids 333–338 of SEQ ID NO:5) regions of human PME-1. The plant homolog(s) of PME-1 can be identified using techniques similar to those described herein, including, but not limited to, the use of sequence database searches in conjunction with PCR, RT-PCR and/or hybridization studies and immunological screening with antibodies specific for a PME-1 protein.

TABLE 1

H59Q and H118Q are catalytically inactive[a]
C subunit-associated phosphatase activity (% wt)[b]

| C subunit | phosphorylase a (Means ± s.d.) | cdc2-phosphorylated Histone H1 (Mean ± s.d.) |
|---|---|---|
| None | 9 ± 2 | 2 ± 1 |
| (vector only control) | | |
| wt | 100 | 100 |
| H59Q | 7 ± 1 | 2 ± 1 |
| H118Q | 8 ± 3 | 2 ± 1 |

[a]PP2A activity present in anti-C subunit (HA tag) immunoprecipitates was measured using phosphorylase a and cdc2-phosphorylated histone H1 as substrates as described herein and normalized to the wt value. The data represent four independent experiments. Background phosphatase activity is probably due to non-specific binding of a small amount of active, non epitope-tagged, endogenous C subunit.

TABLE 2

Nucleotide and Deduced Amino Acid Sequences for Human PME-1
(SEQ ID. NO:4 and SEQ ID NO:5 respectively)

```
GGGCGTCGTTAGGGGAGCGAGTCGTGACCGGTTGGGCCACACTCAACGTGGGACGAAGCT      60

TCGCCTACTGTTTGACTACGTGCGTGCAGCCTCCCCTCGATGTCGGCCCTCGAAAAGAGC     120
                                  |PME-1 coding sequence
                                  |_____
                                    M   S   A   L   E   K   S ATGCACCTCGGCCGCCTTCCCTCTCGCCCACCTCTACCCGGCAGCGGGGGCAGTCAGAGC     180
                 PME-1 coding sequence
 M   H   L   G   R   L   P   S   R   P   P   L   P   G   S   G   G   S   Q   S GGAGCCAAGATGCGAATGGGCCCTGGAAGAAAGCGGGACTTTTCCCCTGTTCCTTGGAGT     240
                 PME-1 coding sequence
 G   A   K   M   R   M   G   P   G   R   K   R   D   F   S   P   V   P   W   S CAGTATTTTGAGTCCATGGAAGATGTAGAAGTAGAGAATGAAACTGGCAAGGATACTTTT     300
                 PME-1 coding sequence
 Q   Y   F   E   S   M   E   D   V   E   V   E   N   E   T   G   K   D   T   F CGAGTCTACAAGAGTGGTTCAGAGGGTCCAGTCCTGCTCCTTCTGCATGGAGGAGGTCAT     360
                 PME-1 coding sequence
 R   V   Y   K   S   G   S   E   G   P   V   L   L   L   L   H   G   G   G   H TCTGCCCTTTCTTGGGCTGTGTTCACGGCAGCGATTATTAGTAGAGTTCAGTGTAGGATT     420
                 PME-1 coding sequence
 S   A   L   S   W   A   V   F   T   A   A   I   I   S   R   V   Q   C   R   I GTAGCTTTGGATCTGCGAAGTCATGGTGAAACAAAGGTCAAGAATCCTGAAGATCTGTCT     480
                 PME-1 coding sequence
 V   A   L   D   L   R   S   H   G   E   T   K   V   K   N   P   E   D   L   S GCAGAAACAATGGCAAAAGACGTTGGCAATGTGGTTGAAGCCATGTATGGGGACCTTCCT     540
                 PME-1 coding sequence
 A   E   T   M   A   K   D   V   G   N   V   V   E   A   M   Y   G   D   L   P

CCTCCAATTATGCTGATTGGACATAGCATGGGTGGTGCTATTGCAGTCCACACAGCATCA     600
```

TABLE 2-continued

Nucleotide and Deduced Amino Acid Sequences for Human PME-1
(SEQ ID. NO:4 and SEQ ID NO:5 respectively)

| PME-1 coding sequence |
|---|
| P  P  I  M  L  I  G  H  S  M  G  G  A  I  A  V  H  T  A  S |

```
TCCAACCTGGTACCAAGCCTCTTGGGTCTGTGCATGATTGATGTTGTAGAAGGTACAGCT    660
                    PME-1 coding sequence
 S    N    L    V    P    S    L    L    G    L    C    M    I    D    V    V    E    G    T    A ATGGATGCACTTAATAGCATGCAGAATTTCTTACGGGGTCGTCCTAAAACCTTCAAGTCT    720
                    PME-1 coding sequence
 M    D    A    L    N    S    M    Q    N    F    L    R    G    R    P    K    T    F    K    S CTGGAGAATGCTATTGAATGGAGTGTGAAGAGTGGCCAGATTCGAAATCTGGAGTCTGCC    780
                    PME-1 coding sequence
 L    E    N    A    I    E    W    S    V    K    S    G    Q    I    R    N    L    E    S    A CGTGTCTCAATGGTTGGCCAAGTCAAACAGTGTGAAGGAATTACAAGTCCAGAAGGCTCA    840
                    PME-1 coding sequence
 R    V    S    M    V    G    Q    V    K    Q    C    E    G    I    T    S    P    E    G    S AAATCTATAGTGGAAGGAATCATAGAGGAAGAAGAAGAAGATGAGGAAGGAAGTGAGTCT    900
                    PME-1 coding sequence
 K    S    I    V    E    G    I    I    E    E    E    E    E    D    E    E    G    S    E    S ATAAGCAAGAGGAAAAAGGAAGATGACATGGAGACCAAGAAAGACCATCCATACACCTGG    960
                    PME-1 coding sequence
 I    S    K    R    K    K    E    D    D    M    E    T    K    K    D    H    P    Y    T    W AGAATTGAACTGGCAAAAACAGAAAAATACTGGGACGGCTGGTTCCGAGGCTTATCCAAT   1020
                    PME-1 coding sequence
 R    I    E    L    A    K    T    E    K    Y    W    D    G    W    F    R    G    L    S    N CTCTTTCTTAGTTGTCCCATTCCTAAATTGCTGCTCTTGGCTGGTGTTGATAGATTGGAT   1080
                    PME-1 coding sequence
 L    F    L    S    C    P    I    P    K    L    L    L    L    A    G    V    D    R    L    D AAAGATCTGACCATTGGCCAGATGCAAGGGAAGTTCCAGATGCAGGTCCTACCCCAGTGT   1140
                    PME-1 coding sequence
 K    D    L    T    I    G    Q    M    Q    G    K    F    Q    M    Q    V    L    P    Q    C GGCCATGCAGTCCATGAGGATGCCCCTGACAAGGTAGCTGAAGCTGTTGCCACTTTCCTG   1200
                    PME-1 coding sequence
 G    H    A    V    H    E    D    A    P    D    K    V    A    E    A    V    A    T    F    L ATCCGGCACAGGTTTGCAGAACCCATCGGTGGATTCCAGTGTGTGTTTCCTGGCTGTTAG   1260
                    PME-1 coding sequence
 I    R    H    R    F    A    E    P    I    G    G    F    Q    C    V    F    P    G    C

TGACCTGCTGTCCACCCCTCCTCAACATCGAGCTCTGTTGTAAATACGTCGCACCAGAGG   1320

CCACTGTGATGCCACTGTCTCCTCTCCATCCCGCCCAGCCATGTGACACTGGCTCCCGGT   1380

AGACGGGCACCCCGAGATGTACCAACCTTTTCATGTATTCTGCCAAAAGCATTGTTTTCC   1440

AGGGCCCTTGACCAACATCGGCTTCCCCAGTCCAGGGCTCCCCTGCTCCTTTCCCTTCCC   1500

TGTACTGGGGTAGCTCCTGCCTGCTCTCCCTGCGTTGCCTAGGGTAAAGCCTCCAGATTT   1560

GCCATACTGAGCCCCTCTTCCTAGCATCAGGCGATACATCTGAGTTCAAATGTCTTCCCA   1620

GGCTCAGGGACCTCCATTCCTTGAGATTGTCTTGGCATGGCCCAGCCCTGCCTCATGGGA   1680

TGGACAATGCATGGGTGGTCTTTATTTTTCCCTTTCAAATAAAACACTAGTCAGGTACC   1740

GTTTTATCCCAGTCGTACTCTTCCAGGTTTGGAAGACCCAGAGAGGCCAAGATCCCATCC   1800

TTAGCCATAGCGAGCGGTGGTGGTGGATAGCATCACAAGAAACGAGCCTGAAAATCAGGT   1860

CCAGCCGGTCCAAGCACATGGCCTCCCATCTGGGAGAGCCCACTGTCCCACTCCCACATG   1920

TCTGGGCACCTGCCCTGGGCTGAGGCCAGGCTGCTCCAGGGGCCTCCTGCGCCCTCACCT   1980

GCCACAGAGCAACCCAGGTTAAATACAGCCCATGCACAAAGCCACAGGCCAAAGCCTATG   2040

GAATTGTTTTTAATCATCAAATTTAACCATTTTCATAACTGGTTCCTGGAGGTGTGCAGT   2100
```

TABLE 2-continued

Nucleotide and Deduced Amino Acid Sequences for Human PME-1
(SEQ ID. NO:4 and SEQ ID NO:5 respectively)

| | |
|---|---|
| GCCCCCTTGCCTCTTCAAACCTACAGCTTCTCTTTGCCATTTGTGGATTTCACATCACTC | 2160 |
| CACACAGAAACATTACAGCCTGGCATCCCCAGTCTTTGCCTTCTTCCAGCTGCCTCGACA | 2220 |
| CAGCACTGTGGCCTGTCCCTATTGCCCAGGCACGCCATTTCCAAGGGCAGGAAGGGGCAG | 2280 |
| TGTCCTGAAGCCCATCTTTTCTGTGACTGTCTTAGGTGATGTGTAGCCCCCTCCACCTTT | 2340 |
| CCACTCAACAACCTCCCACCCCTGTCCTGCTGCATGGTCCGGAGTCTGGGACCTACTTTG | 2400 |
| TTTTTTGTTATTTATGACCTTGTTTAAAGAAAATAAATATGTCCCAACCTTTAAAAAAAA | 2460 |
| AAAAAAAAAAAAAAAAAAAAAAAA | 2484 |

TABLE 3

Saccharomyces cervisiae PME-1 Amino Acid Sequence
(SEQ ID NO:6)

MSDDLRRKIALSQFERAKNVLDATFQEAYEDDENDGDALGSLPSFNGQSNRNRKY

TGKTGSTTDRISSKEKSSLPTWSDFFDNKELVSLPDRDLDVNTYYTLPTSLLSNTTS

IPIFIFHHGAGSSGLSFANLAKELNTKLEGRCGCFAFDARGHAETKFKKADAPICF

DRDSFIKDFVSLLNYWFKSKISQEPLQKVSVILIGHSLGGSICTFAYPKLSTELQKKI

LGITMLDIVEEAATMALNKVEHFLQNTPNVFESINDAVDWHVQHALSRLRSSAEIAI

PALFAPLKSGKVVRITNLKTFSPFWDTWFTDLSHSFVGLPVSKLLILAGNENLDKE

LIVGQMQGKYQLVVFQDSGHFIQEDSPIKTAITLIDFWKRNDSRNVVIKTNWGQHK

TVQNT

From GenBank sequence sequences identified as encoding a hypothetical protein; deposited by JOHNSTON M., ANDREWS S., BRINKMAN R., COOPER J., DING H., DOVER J., DU Z., FAVELLO A., FULTON L., GATTUNG S., GEISEL C., KIRSTEN J., KUCABA T., HILLIER, L., JIER M., JOHNSTON L., LANGSTON Y., ATREILLE P., LOUIS E. J., MACRI C., MARDIS E., MENEZES S., MOUSER L., NHAN M., RIFKIN L., RILES L., ST.PETER H., TREVASKIS E., VAUGHAN K., VIGNATI D., WILCOX L., WOHLDMAN P., WATERSTON R., WILSON R., VAUDIN M.; See also SCIENCE 265:2077–2082(1994). ACCESSION: P38796; PIR: S46814 #type complete ACCESSION: S46814 GB: YSCH9205 ACCESSION: U10556 DESC HYPOTHETICAL 44.9 KD PROTEIN IN ERG7-NMD2 INTERGENIC REGION. DATE FEB. 1, 1995 (REL. 31, CREATED) FEB. 1, 1995 (REL. 31, LAST SEQUENCE UPDATE) FEB. 1, 1995 (REL. 31, LAST ANNOTATION UPDATE) GENE YHR075C. #map_ position 8R COM SEQUENCE FROM N.A. STRAIN= S288C/AB972; MED MEDLINE; 94378003. AUTH TAXONOMY EUKARYOTA; FUNGI; ASCOMYCOTINA; HEMIASCOMYCETES. COMMENT Nucleic Acid Features translated to generate this entry: CDS complement (9569 . . . 10771) /codon_start=1/evidence=not_ experimental/db_xref="PID:g500835"

TABLE 4

Caenorhabditis elegans PME-1 Amino Acid Sequence.
(SEQ ID NO:7)

MSDDKLDTLPDLQSETSHVTTPHRQNDLLRQAVTHGRPPPVPSTSTSGKKREMSEL

PWSDFFDEKKDANIDGDVFNVYIKGNEGPIFYLLHGGGYSGLTWACFAKELATLI

SCRVVAPDLRGHGDTKCSDEHDLSKETQIKDIGAIFKNIFGEDDSPVCIVGHSMGG

ALAIHTLNAKMISSKVAALIVIDVVEGSAMEALGGMVHFLHSRPSSFPSIEKAIHWC

LSSGTARNPTAARVSMPSQIREVSEHEYTWRIDLTTTEQYWKGWFEGLSKEFLGCS

TABLE 4-continued

Caenorhabditis elegans PME-1 Amino Acid Sequence.
(SEQ ID NO:7)

VPKMLVLAGVDRLDRDLTIGQMQGKFQTCVLPKVGHCVQEDSPQNLADEVGRFA

CRHRIAQPKFSALASPPDPAILEYRKRIHHQ

TABLE 5

Partial CDNA Sequence of Mus musculus PME-1 homolog
(SEQ ID NO:8)

TTGTACTGCACGTATCGTGGGACGGACCTTGGGCCACTGTTGTCGACGTGCGG

CCTCCCTTTGATGTCGGCCCTTGAAAAAAGCATGCACCTCGGCCGCCTACCTTC

TCGCCCTCCTCTACCCGGCAGCGGGGGCAGTCAGAGCGGACGCAAGATGCGG

ATGGGCCCTGGACGGAAGCGGGACTTTACCCCTGTCCCATGGAGTCAGTACTT

TGAGTCAATGGAAGATGTGGAAGTGGAGAATGAAACTGGCAAGGATACTTTTC

GAGTTTACAAGATTGGTTXXXXXXXXXXXXXXXXXXXXXXXXXXXXXXX

XXXXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXXXX

XTTCGGATCCTTGGCCAAGTCAAACAGTGTGAAGGAATTACAAGTCCAGAAGG

TTCCAAATCCATAGTGGAAGGAATCATAGAGGAGGAGGAAGAAGATGAGGAA

GGAAGTGAGTCAGTTAACAAGAGGAAAAAGGAAGACGACATGGAAACCAAGA

AGGATCACCCATACACCTGGAGAATTGAGCTGGCAAAAACAGAAAAGTACTGG

GATGGCTGGTTCCGGGGCTTATCCAATCTCTTTCTTAGCTGTCCTATTCCTAAAC

TGCTGCTCTTGGCGGGTGTTGACAGATTGGATAAAGATCTGACCATAGGCCAG

ATGCAGGGGAAGTTCCAGATGCAGGTCTTACCCCAGTGTGGCCATGCAGTCCA

TGAGGATGCCCCTGACAAGGTAGCTGAAGCTGTTGCCACTTTCCTGATCCGGC

ACAGGTTTGCAGAGCCCATCGGAGGATTCCAGTGTGTGTTTACTGGCTGCTAG

TGACCTGCTGTCTACTCCTCCCTCTACATTGAGCTCTGTTGTAAATACATCGCAC

CAGAGGCCACTGTGACGCCGCTGTCTCCTCCTCTCCATCCCGCCCAGCCATGT

GACACCGGCTCTTGTAGAGGGCATCCCCAGATGTCCAAACCCTTTCCTGTGTAC

TGTTGAAAGCATTGTTCTTCAGGGCCCTTGTCCAACAGTGGCCCGTGCAGTCTG

GGGTCCACAGCTCTTCCTCTCCTTCCTGTGCTCCCTGCCTTGCCTAGGATGAAG

CCTCCAGCGCTGCTCCCTGGCCCTGTTCCTGGCATATGGCAATGTACCCCAGG

CTCAGGGATCTCCCTTCCTTGAGGATGTTCTTGGCATGGTCCTGCCCTACCTCA

TGGGATGGGCAATGCACACACTGGCCCTTATTTTTCCCTTTCAAATAAAACACC

TABLE 5-continued

Partial CDNA Sequence of *Mus musculus* PME-1 homolog
(SEQ ID NO:8)

AGTCAGGTACCTTTATCCCAGTCTTAACTGTCCCAAATCTGGAAGGTCCAGAGT

AAGCAGGATTCAGGGAGAGGGAGTGGATAGCAAGTATCCCAAGAAACCAACC

TGTAAGTCAGGTCCAGCCAGTCCAAGCACATGGCTTCCCATCTGGGTGAGCCC

ACTGTCCCACTCCCACATGTCTGGGCACCTGCCCTGGGCTGAGGCCAGGCTGC

TCCAAGGGCCGCATGAGCCCTAATCTGCCACAGAGCAACCCAGGTTAAACACA

GCCCATGCACAAAGCCACAGGCTAAATCCTGTGGAATTGTTTTTAATGACTGAA

TTTAACCATTTTCATAGTTGGTTCCTGGAGGTGTGCCAAGTGCCCGCTTGCCTC

TTCTAGACCCACAGCTTCTTGATCCACTTGTGGTTTCCATGTCACTAATGTAGAA

ACATCATGGACTAGCATCCCCAGTCTTTGCCCTCATCCAGCTGTCGCAGCGCAC

ACTGGGGCCTCCCCCTGCTGCCCAGGGGGGRCGGGGTGGGCAGCCTCCTGA

AACCCATCTTTCTGTGACTGTCTTAGGTGACGTGTAGCCCTCTTCCGTTTTTCA

CCCAACAACTTCCTCTGTCCTGCTGCACGGTCCAGAGTCTGGGACCGACTTTGT

TTCTTTGTTATTTATGATCTTGTTTAAAGAAAATAAATATCTCCCAACCTTTAAAA

AAAAAAAAAAAAAAAAAAAAAAAAAAAAAAAAAAAAAAAAAAAAAAAAAAA

A

TABLE 6

*S. cerevisiae* PME-1 Coding Sequence
(SEQ ID NO:9)

ATGTCTGACGATTTGAGAAGAAAAATTGCTTTATCCCAGTTTGAGAGAGCCAAG

AATGTTCTAGATGCGACATTCCAAGAAGCATACGAGGATGATGAAAACGATGG

TGATGCATTAGGTTCCCTGCCATCATTTAATGGACAATCAATAGGAACAGAAA

ATATACGGGCAAAACCGGTAGTACTACTGATAGAATTTCAAGTAAGGAAAAGA

GTAGTTTACCCACTTGGAGTGATTTTTTTGATAATAAGGAGTTGGTAAGTCTTCC

TGATAGAGATCTGGACGTAAATACATACTATACATTACCTACTTCATTGTTATCA

AATACCACTTCAATTCCCATCTTTATTTTCCACCATGGGGCGGGCTCCTCAGGTT

TATCATTTGCAAACTTGGCCAAGGAATTAAATACTAAACTAGAAGGAAGATGCG

GATGCTTTGCATTTGATGCTAGGGGCATGCAGAAACAAAGTTTAAGAAGGCT

GATGCGCCTATATGCTTTGACAGGGACTCTTTTATCAAAGATTTTGTAAGCCTG

CTAAATTATTGGTTTAAGTCTAAAATAAGCCAAGAGCCACTTCAGAAGGTATCT

GTTATACTAATTGGTCATTCCCTTGGTGGAAGTATATGTACTTTTGCGTACCCTA

AATTATCAACAGAACTACAAAAGAAAATTCTTGGTATTACTATGTTAGATATTGT

AGAAGAGGCTGCCATTATGGCCTTAAATAAAGTTGAACATTTTTTGCAGAATAC

ACCCAATGTATTTGAATCAATTAATGACGCTGTCGATTGGCACGTTCAACACGC

GTTATCGAGATTGAGGTCAAGCGCCGAAATTGCTATACCAGCTTTATTTGCTCC

GCTCAAGTCAGGGAAAGTTGTCAGGATAACAAACCTTAAGACCTTTAGCCCTTT

CTGGGACACATGGTTTACCGATCTGTCGCACTCCTTTGTTGGCTTACCTGTTAG

TAAATTATTAATATTGGCGGGAAACGAAAATCTCGATAAAGAATTAATTGTGGG

TABLE 6-continued

S. cerevisiae PME-1 Coding Sequence
(SEQ ID NO:9)

GCAAATGCAAGGTAAATATCAGTTGGTAGTTTTCCAAGATTCCGGGCATTTCAT

TCAAGAAGATTCGCCTATAAAAACAGCAATCACTTTAATTGATTTCTGGAAGCG

GAACGATTCTAGGAATGTAGTAATCAAGACTAATTGGGGTCAACACAAAACCGT

GCAAAATACATAA

TABLE 7

C. elegans PME-1 Coding Sequence
(SEQ ID NO:10)

ATGTCCGACGATAAATTAGACACTCTTCCGGATCTTCAATCGGAAACGTCACAT

GTCACAACTCCTCACAGGCAAAATGATCTTCTTCGTCAAGCGGTCACTCATGGA

AGGCCACCACCAGTTCCGAGCACATCAACTTCTGGAAAGAAACGAGAAATGTC

TGAACTACCGTGGTCAGATTTTTTTGATGAAAAGAAGGACGCAAACATTGATGG

AGATGTTTTCAATGTGTACATAAAGGGAAATGAAGGTCCAATTTTCTATTTGCTT

CACGGTGGAGGTTATTCAGGCCTCACATGGGCGTGTTTTGCGAAAGAATTGGC

AACTTTAATATCATGCAGAGTTGTTGCACCTGATTTAAGAGGACACGGCGACAC

TAAATGTTCTGATGAGCACGATCTTTCGAAAGAAACCCAAATAAAGGATATTGG

AGCAATCTTCAAGAACATTTTCGGCGAAGACGATTCACCAGTATGCATTGTTGG

ACACAGTATGGGTGGTGCATTGGCCATTCATACATTGAATGCAAAGATGATTTC

TTCAAAAGTCGCTGCACTCATTGTCATTGATGTTGTCGAAGGTTCCGCTATGGA

AGCACTTGGAGGAATGGTTCATTTTTTACATTCAAGGCCTTCTTCATTTCCTTCT

ATCGAAAAAGCCATTCACTGGTGCCTTTCTTCGGGTACAGCGAGGAATCCCACA

GCTGCACGGGTCTCAATGCCGTCTCAAATTAGAGAAGTATCGGAACACGAGTA

CACTTGGCGAATTGATTTAACAACAACAGAACAGTACTGGAAAGGATGGTTTGA

AGGATTATCCAAAGAATTTTTGGGATGTTCCGTTCCGAAGATGCTTGTTCTAGC

GGGCGTTGATCGGCTGGACAGGGATCTCACAATTGGTCAAATGCAGGGAAAGT

TTCAGACTTGTGTGTTACCAAAAGTTGGACATTGTGTTCAGGAAGATAGCCCAC

AAAATCTTGCAGATGAAGTCGGAAGATTCGCTTGCCGCCATAGAATTGCCCAAC

CGAAATTCTCAGCCCTTGCATCACCACCAGATCCAGCGATTCTCGAATACAGAA

AACGTCATCACCAATAA

TABLE 8

Comparison of the sequences surrounding the putative or known active site serines of PME-1 proteins and CheB

| Species | First residue sh | Sequence | SEQ ID NO: |
|---|---|---|---|
| Human PME-1 | 150 | IM<u>LIGHS</u>MG | 11 |
| C. elegans PME-1 | 158 | VC<u>IVGHS</u>MG | 12 |
| S. cerevisiae PME-1 | 199 | VI<u>LIGHS</u>LG | 13 |
| S. typhimurium CheB | 158 | LI<u>AIGAS</u>TG | 14 |

The PME-1 and CheB residues matching the signature motif ([LIV]-x-[LIVFY]-[LIVST]-G-[HYWV]-S-x-G-[GSTAC]) (SEQ ID NO:15) for lipases utilizing an active site serine are underlined. The serine present in each sequence is the predicted (PME-1) or known (CheB) active site serine.

TABLE 9

Alignment of human, C. elegans and S. cerevisiae PME-1 protein sequences
(SEQ ID NO:5, SEQ ID NO:7, and SEQ ID:6 respectively)

```
  1  M S A - - - - L E K S M H L G R L P S - - R P P L P G    Human
  1  M S D D - - K L D T L P D L Q S E T S - - H V T T P H    C. elegans
  1  M S D D L R R K I A L S Q F E R A K N V L D A T F Q E    S. cerevisiae 22  S G G S - - - Q S G A K M R M G P - - - - - - - G R K    Human
 24  R Q N D L L R Q A V T H G R P P P V P S T S T S G K K    C. elegans
 28  A Y E D D E N D G D A L G S L P S F N G Q S N R N R K    S. cerevisiae 39  - - - - - - - - - - - - - R D F S P V P - W S Q Y F      Human
 51  - - - - - - - - - - - - - R E M S E L P - W S D F F      C. elegans
 55  Y T G K T G S T T D R I S S K E K S S L P T W S D F F    S. cerevisiae 51  E S M E D V E V - E N E T G K D T F - - - - - R V Y K    Human
 63  D E K K D A N I - D G - - - - D V F - - - - - N V Y I    C. elegans
 82  D N K E L V S L P D R D L D V N T Y Y T L P T S L L S    S. cerevisiae 72  S G S E G P V L L L L H G G H S A L S W A V F T A A      Human
 80  K G N E G P I F Y L L H G G Y S G L T W A C F A K E      C. elegans
109  N T T S I P I F I F H H G A G S S G L S F A N L A K E    S. cerevisiae 99  I I S R V Q - - C R I V A L D L R S H G E T K V K N P    Human
107  L A T L I S - - C R V V A P D L R G H G D T K C S D E    C. elegans
136  L N T K L E G R C G C F A F D A R G H A E T K F K K A    S. cerevisiae 124  E D - - - L S A E T M A K D V G N V V E A M Y G D L P    Human
132  H D - - - L S K E T Q I K D I G A I F K N I F G E D D    C. elegans
163  D A P I C F D R D S F I K D F V S L L N Y W F K S K I    S. cerevisiae 148  P - - - - - - - P I M L I G H S M G G A I - - - A V H    Human
156  S - - - - - - - P V C I V G H S M G G A L - - - A I H    C. elegans
190  S Q E P L Q K V S V I L I G H S L G G S I C T F A Y P    S. cerevisiae 165  T A S S N L V P S - L G L C M I D V V E G T A M D A      Human
173  T L N A K M I S S K V A A L I V I D V V E G S A M E A    C. elegans
217  K L S T E L - Q K K I L G I T M L D I V E E A A I M A    S. cerevisiae 191  L N S M Q N F L R G R P K T F K S L E N A I E W S V K    Human
200  L G G M V H F L H S R P S S F P S I E K A I H W C L S    C. elegans
243  L N K V E H F L Q N T P N V F E S I N D A V D W H V Q    S. cerevisiae
```

TABLE 9-continued

Alignment of human, *C. elegans* and *S. cerevisiae* PME-1 protein sequences
(SEQ ID NO:5, SEQ ID NO:7, and SEQ ID:6 respectively)

```
218  S G Q I R N L E S A R V S M V G Q V K Q C E G I T S P           Human
227  S G T A R N P T A A R V S M P S Q I R E V S - - - - -           C. elegans
270  H A L S R L R S S A E I A I P A - - - - - - - L F A P           S. cerevisiae 245  E G S K S I V E G I I E E E E E D E E G S E S I S K R           Human
249  - - - - - - - - - - - - - - - - - - - - - - - - - -           C. elegans
290  L K S G K V V - - - - - - - - - - - - - - - - - - -           S. cerevisiae 272  K K E D D M E T K K D H P Y T W R I E L A K T E K Y W           Human
249  - - - - - - - - - - E H E Y T W R I D L T T T E Q Y W           C. elegans
297  - - - - - - - - - - - - - - R I T N L K T F S P F W           S. cerevisiae 299  D G W F R G L S N L F L S C P I P K L L L A G V D R             Human
266  K G W F E G L S K E F L G C S V P K M L V A G V D R             C. elegans
309  D T W F T D L S H S F V G L P V S K L L I L A G N E N           S. cerevisiae 326  L D K D L T I G Q M Q G K F Q M Q V L P Q C G H A V H           Human
293  L D R D L T I G Q M Q G K F Q T C V L P K V G H C V Q           C. elegans
336  L D K E L I V G Q M Q G K Y Q L V V F Q D S G H F I Q           S. cerevisiae 353  E D A P D K V A E A V A T F L I R H R F A E P - - - -           Human
320  E D S P Q N L A D E V G R F A C R H R I A Q P K F S A           C. elegans
363  E D S P I K T A I T L I D F W K R N D S R N V V I K T           S. cerevisiae 376  - - - - - - - - I G G F Q C V F P G C                           Human
347  L A S P P D P A I L E Y R K R H H Q                             C. elegans
390  - - - - - - - - N W G Q H K T V Q N T                           S. cerevisiae
```

We claim:

1. An isolated and purified polypeptide comprising the amino acid sequence as given in SEQ ID NO:5.

2. An immunogenic composition comprising one or more antigenic components, said antigenic component is either an antigenic peptide linked to a carrier molecule to form a peptide-carrier complex or a multiantigenic peptide molecule having a plurality of antigenic peptides of identical amino acid sequence, wherein the amino acid sequence of the antigenic peptide consists of amino acids 288–303 of SEQ ID NO:5.

* * * * *

UNITED STATES PATENT AND TRADEMARK OFFICE
CERTIFICATE OF CORRECTION

PATENT NO. : 6,528,295 B2
DATED : March 4, 2003
INVENTOR(S) : Pallas et al.

It is certified that error appears in the above-identified patent and that said Letters Patent is hereby corrected as shown below:

Column 5,
Line 62, replace "(H590Q," with -- (H59Q, --.

Column 12,
Line 16, replace "MRNA" with -- mRNA --.
Line 49, replace "D1S916-D11S911" with -- D11S916-D11S911 --.

Column 29,

Next to the last line of Table 2, replace
"TTTTTTGTTATTTATGACCTTGTTTAAAGAAAATAAATATGTCCCAACCTTTAAAAAAAA" with

-- TTTTTTGTTATTT ATGACCTTGTTTAAAGAAAATAAATATCTCCCAACCTTTAAAAAAAA--.

Line 5, in Table 3, replace the first 15 amino acid residues with
-- LGITMLDIVEEAAIM --.

Column 33,
Next to the last line of Table 5, add one more -- A -- at the end of the row of A residues.

The third line of Table 6 , replace
"TGATGCATTAGGTTCCCTGCCATCATTTAATGGACAATCAATAGGAACAGAAA" with

-- TGATGCATTAGGTTCCCTGCCATCATTTAATGGACAATCAAATAGGAACAGAAA--.

Signed and Sealed this

Fifth Day of August, 2003

JAMES E. ROGAN
*Director of the United States Patent and Trademark Office*

SEQUENCE LISTING

<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
tgttgaggag gggtggacag                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
tgtatgggga ccttcctcct                                              20

```
<210> SEQ ID NO 3
<211> LENGTH: 16
<212> TYPE: PRT
<213> ORGANISM: Homo sapiens

<400> SEQUENCE: 3

Arg Ile Glu Leu Ala Lys Thr Glu Lys Tyr Trp Asp Gly Trp Phe Arg
 1               5                  10                  15

<210> SEQ ID NO 4
<211> LENGTH: 2484
<212> TYPE: DNA
<213> ORGANISM: Homo sapiens
<220> FEATURE:
<221> NAME/KEY: CDS
<222> LOCATION: (100)..(1257)

<400> SEQUENCE: 4
gggcgtcgtt aggggagcga gtcgtgaccg gttgggccac actcaacgtg ggacgaagct      60
tcgcctactg tttgactacg tgcgtgcagc ctcccctcg atg tcg gcc ctc gaa        114
                                            Met Ser Ala Leu Glu
                                             1               5 aag agc atg cac ctc ggc cgc ctt ccc tct cgc cca cct cta ccc ggc       162
Lys Ser Met His Leu Gly Arg Leu Pro Ser Arg Pro Pro Leu Pro Gly
             10                  15                  20 agc ggg ggc agt cag agc gga gcc aag atg cga atg ggc cct gga aga       210
Ser Gly Gly Ser Gln Ser Gly Ala Lys Met Arg Met Gly Pro Gly Arg
         25                  30                  35 aag cgg gac ttt tcc cct gtt cct tgg agt cag tat ttt gag tcc atg       258
Lys Arg Asp Phe Ser Pro Val Pro Trp Ser Gln Tyr Phe Glu Ser Met
     40                  45                  50 gaa gat gta gaa gta gag aat gaa act ggc aag gat act ttt cga gtc       306
Glu Asp Val Glu Val Glu Asn Glu Thr Gly Lys Asp Thr Phe Arg Val
 55                  60                  65 tac aag agt ggt tca gag ggt cca gtc ctg ctc ctt ctg cat gga gga       354
Tyr Lys Ser Gly Ser Glu Gly Pro Val Leu Leu Leu Leu His Gly Gly
 70                  75                  80                  85 ggt cat tct gcc ctt tct tgg gct gtg ttc acg gca gcg att att agt       402
Gly His Ser Ala Leu Ser Trp Ala Val Phe Thr Ala Ala Ile Ile Ser
             90                  95                 100 aga gtt cag tgt agg att gta gct ttg gat ctg cga agt cat ggt gaa       450
Arg Val Gln Cys Arg Ile Val Ala Leu Asp Leu Arg Ser His Gly Glu
        105                 110                 115 aca aag gtc aag aat cct gaa gat ctg tct gca gaa aca atg gca aaa       498
Thr Lys Val Lys Asn Pro Glu Asp Leu Ser Ala Glu Thr Met Ala Lys
    120                 125                 130 gac gtt ggc aat gtg gtt gaa gcc atg tat ggg gac ctt cct cct cca       546
Asp Val Gly Asn Val Val Glu Ala Met Tyr Gly Asp Leu Pro Pro Pro
135                 140                 145 att atg ctg att gga cat agc atg ggt ggt gct att gca gtc cac aca       594
Ile Met Leu Ile Gly His Ser Met Gly Gly Ala Ile Ala Val His Thr
150                 155                 160                 165 gca tca tcc aac ctg gta cca agc ctc ttg ggt ctg tgc atg att gat       642
Ala Ser Ser Asn Leu Val Pro Ser Leu Leu Gly Leu Cys Met Ile Asp
            170                 175                 180 gtt gta gaa ggt aca gct atg gat gca ctt aat agc atg cag aat ttc       690
Val Val Glu Gly Thr Ala Met Asp Ala Leu Asn Ser Met Gln Asn Phe
        185                 190                 195 tta cgg ggt cgt cct aaa acc ttc aag tct ctg gag aat gct att gaa       738
Leu Arg Gly Arg Pro Lys Thr Phe Lys Ser Leu Glu Asn Ala Ile Glu
    200                 205                 210
```

-continued

| | |
|---|---|
| tgg agt gtg aag agt ggc cag att cga aat ctg gag tct gcc cgt gtc<br>Trp Ser Val Lys Ser Gly Gln Ile Arg Asn Leu Glu Ser Ala Arg Val<br>215                 220                       225 | 786 |
| tca atg gtt ggc caa gtc aaa cag tgt gaa gga att aca agt cca gaa<br>Ser Met Val Gly Gln Val Lys Gln Cys Glu Gly Ile Thr Ser Pro Glu<br>230                 235                    240                 245 | 834 |
| ggc tca aaa tct ata gtg gaa gga atc ata gag gaa gaa gaa gaa gat<br>Gly Ser Lys Ser Ile Val Glu Gly Ile Ile Glu Glu Glu Glu Glu Asp<br>             250                    255                    260 | 882 |
| gag gaa gga agt gag tct ata agc aag agg aaa aag gaa gat gac atg<br>Glu Glu Gly Ser Glu Ser Ile Ser Lys Arg Lys Lys Glu Asp Asp Met<br>265                 270                    275 | 930 |
| gag acc aag aaa gac cat cca tac acc tgg aga att gaa ctg gca aaa<br>Glu Thr Lys Lys Asp His Pro Tyr Thr Trp Arg Ile Glu Leu Ala Lys<br>280                 285                    290 | 978 |
| aca gaa aaa tac tgg gac ggc tgg ttc cga ggc tta tcc aat ctc ttt<br>Thr Glu Lys Tyr Trp Asp Gly Trp Phe Arg Gly Leu Ser Asn Leu Phe<br>295                 300                    305 | 1026 |
| ctt agt tgt ccc att cct aaa ttg ctc ttg gct ggt gtt gat aga<br>Leu Ser Cys Pro Ile Pro Lys Leu Leu Leu Ala Gly Val Asp Arg<br>310                 315                    320                325 | 1074 |
| ttg gat aaa gat ctg acc att ggc cag atg caa ggg aag ttc cag atg<br>Leu Asp Lys Asp Leu Thr Ile Gly Gln Met Gln Gly Lys Phe Gln Met<br>             330                    335                    340 | 1122 |
| cag gtc cta ccc cag tgt ggc cat gca gtc cat gag gat gcc cct gac<br>Gln Val Leu Pro Gln Cys Gly His Ala Val His Glu Asp Ala Pro Asp<br>345                 350                    355 | 1170 |
| aag gta gct gaa gct gtt gcc act ttc ctg atc cgg cac agg ttt gca<br>Lys Val Ala Glu Ala Val Ala Thr Phe Leu Ile Arg His Arg Phe Ala<br>360                 365                    370 | 1218 |
| gaa ccc atc ggt gga ttc cag tgt gtg ttt cct ggc tgt tagtgacctg<br>Glu Pro Ile Gly Gly Phe Gln Cys Val Phe Pro Gly Cys<br>375                 380                    385 | 1267 |
| ctgtccaccc tcctcaaca tcgagctctg ttgtaaatac gtcgcaccag aggccactgt | 1327 |
| gatgccactg tctcctctcc atcccgccca gccatgtgac actggctccc ggtagacggg | 1387 |
| caccccgaga tgtaccaacc ttttcatgta ttctgccaaa gcattgttt tccagggccc | 1447 |
| ttgaccaaca tcggcttccc cagtccaggg ctcccctgct cctttccctt ccctgtactg | 1507 |
| gggtagctcc tgcctgctct ccctgcgttg cctagggtaa agcctccaga tttgccatac | 1567 |
| tgagcccctc ttcctagcat caggcgatac atctgagttc aaatgtcttc ccaggctcag | 1627 |
| ggacctccat tccttgagat tgtcttggca tggcccagcc ctgcctcatg ggatggacaa | 1687 |
| tgcatggggt ggtctttatt tttccctttc aaataaaaca ctagtcaggt accgttttat | 1747 |
| cccagtcgta ctcttccagg tttggaagac ccagagaggc caagatccca tccttagcca | 1807 |
| tagcgagcgg tggtggtgga tagcatcaca agaaacgagc tgaaaatca ggtccagccg | 1867 |
| gtccaagcac atggcctccc atctggagag ccccactgtc ccactcccac atgtctgggc | 1927 |
| acctgccctg ggctgaggcc aggctgctcc aggggcctcc tgcgcccctca cctgccacag | 1987 |
| agcaacccag gttaaataca gcccatgcac aaagccacag gccaaagcct atggaattgt | 2047 |
| ttttaatcat caaatttaac catttcata actggttcct ggaggtgtgc agtgcccct | 2107 |
| tgcctcttca aacctacagc ttctctttgc catttgtgga tttcacatca ctccacacag | 2167 |
| aaacattaca gcctggcatc cccagtcttt gccttcttcc agctgcctcg acacagcact | 2227 |
| gtggcctgtc cctattgccc aggcacgcca tttccaaggg caggaagggg cagtgtcctg | 2287 |
| aagcccatct tttctgtgac tgtcttaggt gatgtgtagc ccctccacc tttccactca | 2347 |

-continued

```
acaacctccc accctgtcc tgctgcatgg tccggagtct gggacctact ttgtttttg    2407 ttatttatga ccttgtttaa agaaataaa tatctcccaa cctttaaaaa aaaaaaaaa    2467 aaaaaaaaaa aaaaaaa                                                 2484
```

<210> SEQ ID NO 5
<211> LENGTH: 386
<212> TYPE: PRT
<213> ORGANISM: Homo sapiens

<400> SEQUENCE: 5

```
Met Ser Ala Leu Glu Lys Ser Met His Leu Gly Arg Leu Pro Ser Arg
 1               5                  10                  15

Pro Pro Leu Pro Gly Ser Gly Gly Ser Gln Ser Gly Ala Lys Met Arg
            20                  25                  30

Met Gly Pro Gly Arg Lys Arg Asp Phe Ser Pro Val Pro Trp Ser Gln
        35                  40                  45

Tyr Phe Glu Ser Met Glu Asp Val Glu Val Glu Asn Glu Thr Gly Lys
    50                  55                  60

Asp Thr Phe Arg Val Tyr Lys Ser Gly Ser Glu Gly Pro Val Leu Leu
65                  70                  75                  80

Leu Leu His Gly Gly Gly His Ser Ala Leu Ser Trp Ala Val Phe Thr
                85                  90                  95

Ala Ala Ile Ile Ser Arg Val Gln Cys Arg Ile Val Ala Leu Asp Leu
            100                 105                 110

Arg Ser His Gly Glu Thr Lys Val Lys Asn Pro Glu Asp Leu Ser Ala
        115                 120                 125

Glu Thr Met Ala Lys Asp Val Gly Asn Val Val Glu Ala Met Tyr Gly
    130                 135                 140

Asp Leu Pro Pro Ile Met Leu Ile Gly His Ser Met Gly Gly Ala
145                 150                 155                 160

Ile Ala Val His Thr Ala Ser Ser Asn Leu Val Pro Ser Leu Leu Gly
                165                 170                 175

Leu Cys Met Ile Asp Val Val Glu Gly Thr Ala Met Asp Ala Leu Asn
            180                 185                 190

Ser Met Gln Asn Phe Leu Arg Gly Arg Pro Lys Thr Phe Lys Ser Leu
        195                 200                 205

Glu Asn Ala Ile Glu Trp Ser Val Lys Ser Gly Gln Ile Arg Asn Leu
    210                 215                 220

Glu Ser Ala Arg Val Ser Met Val Gly Gln Val Lys Gln Cys Glu Gly
225                 230                 235                 240

Ile Thr Ser Pro Glu Gly Ser Lys Ser Ile Val Glu Gly Ile Ile Glu
                245                 250                 255

Glu Glu Glu Glu Asp Glu Glu Gly Ser Glu Ser Ile Ser Lys Arg Lys
            260                 265                 270

Lys Glu Asp Asp Met Glu Thr Lys Lys Asp His Pro Tyr Thr Trp Arg
        275                 280                 285

Ile Glu Leu Ala Lys Thr Glu Lys Tyr Trp Asp Gly Trp Phe Arg Gly
    290                 295                 300

Leu Ser Asn Leu Phe Leu Ser Cys Pro Ile Pro Lys Leu Leu Leu Leu
305                 310                 315                 320

Ala Gly Val Asp Arg Leu Asp Lys Asp Leu Thr Ile Gly Gln Met Gln
                325                 330                 335

Gly Lys Phe Gln Met Gln Val Leu Pro Gln Cys Gly His Ala Val His
```

```
                    340                 345                 350
Glu Asp Ala Pro Asp Lys Val Ala Glu Ala Val Ala Thr Phe Leu Ile
                355                 360                 365
Arg His Arg Phe Ala Glu Pro Ile Gly Gly Phe Gln Cys Val Phe Pro
            370                 375                 380
Gly Cys
385

<210> SEQ ID NO 6
<211> LENGTH: 400
<212> TYPE: PRT
<213> ORGANISM: Saccharomyces cerevisiae

<400> SEQUENCE: 6

Met Ser Asp Asp Leu Arg Arg Lys Ile Ala Leu Ser Gln Phe Glu Arg
  1               5                  10                  15
Ala Lys Asn Val Leu Asp Ala Thr Phe Gln Glu Ala Tyr Glu Asp Asp
                 20                  25                  30
Glu Asn Asp Gly Asp Ala Leu Gly Ser Leu Pro Ser Phe Asn Gly Gln
             35                  40                  45
Ser Asn Arg Asn Arg Lys Tyr Thr Gly Lys Thr Gly Ser Thr Thr Asp
         50                  55                  60
Arg Ile Ser Ser Lys Glu Lys Ser Ser Leu Pro Thr Trp Ser Asp Phe
 65                  70                  75                  80
Phe Asp Asn Lys Glu Leu Val Ser Leu Pro Asp Arg Asp Leu Asp Val
                 85                  90                  95
Asn Thr Tyr Tyr Thr Leu Pro Thr Ser Leu Leu Ser Asn Thr Thr Ser
            100                 105                 110
Ile Pro Ile Phe Ile Phe His His Gly Ala Gly Ser Ser Gly Leu Ser
        115                 120                 125
Phe Ala Asn Leu Ala Lys Glu Leu Asn Thr Lys Leu Glu Gly Arg Cys
    130                 135                 140
Gly Cys Phe Ala Phe Asp Ala Arg Gly His Ala Glu Thr Lys Phe Lys
145                 150                 155                 160
Lys Ala Asp Ala Pro Ile Cys Phe Asp Arg Asp Ser Phe Ile Lys Asp
                165                 170                 175
Phe Val Ser Leu Leu Asn Tyr Trp Phe Lys Ser Lys Ile Ser Gln Glu
            180                 185                 190
Pro Leu Gln Lys Val Ser Val Ile Leu Ile Gly His Ser Leu Gly Gly
        195                 200                 205
Ser Ile Cys Thr Phe Ala Tyr Pro Lys Leu Ser Thr Glu Leu Gln Lys
    210                 215                 220
Lys Ile Leu Gly Ile Thr Met Leu Asp Ile Val Glu Glu Ala Ala Ile
225                 230                 235                 240
Met Ala Leu Asn Lys Val Glu His Phe Leu Gln Asn Thr Pro Asn Val
                245                 250                 255
Phe Glu Ser Ile Asn Asp Ala Val Asp Trp His Val Gln His Ala Leu
            260                 265                 270
Ser Arg Leu Arg Ser Ser Ala Glu Ile Ala Ile Pro Ala Leu Phe Ala
        275                 280                 285
Pro Leu Lys Ser Gly Lys Val Val Arg Ile Thr Asn Leu Lys Thr Phe
    290                 295                 300
Ser Pro Phe Trp Asp Thr Trp Phe Thr Asp Leu Ser His Ser Phe Val
305                 310                 315                 320
```

```
Gly Leu Pro Val Ser Lys Leu Ile Leu Ala Gly Asn Glu Asn Leu
                325                 330                 335

Asp Lys Glu Leu Ile Val Gly Gln Met Gln Gly Lys Tyr Gln Leu Val
                340                 345                 350

Val Phe Gln Asp Ser Gly His Phe Ile Gln Glu Asp Ser Pro Ile Lys
                355                 360                 365

Thr Ala Ile Thr Leu Ile Asp Phe Trp Lys Arg Asn Asp Ser Arg Asn
                370                 375                 380

Val Val Ile Lys Thr Asn Trp Gly Gln His Lys Thr Val Gln Asn Thr
385                 390                 395                 400

<210> SEQ ID NO 7
<211> LENGTH: 364
<212> TYPE: PRT
<213> ORGANISM: Caenorhabditis elegans

<400> SEQUENCE: 7

Met Ser Asp Asp Lys Leu Asp Thr Leu Pro Asp Leu Gln Ser Glu Thr
1               5                   10                  15

Ser His Val Thr Thr Pro His Arg Gln Asn Asp Leu Leu Arg Gln Ala
                20                  25                  30

Val Thr His Gly Arg Pro Pro Val Pro Ser Thr Ser Thr Ser Gly
                35                  40                  45

Lys Lys Arg Glu Met Ser Glu Leu Pro Trp Ser Asp Phe Phe Asp Glu
    50                  55                  60

Lys Lys Asp Ala Asn Ile Asp Gly Asp Val Phe Asn Val Tyr Ile Lys
65                  70                  75                  80

Gly Asn Glu Gly Pro Ile Phe Tyr Leu Leu His Gly Gly Gly Tyr Ser
                85                  90                  95

Gly Leu Thr Trp Ala Cys Phe Ala Lys Glu Leu Ala Thr Leu Ile Ser
                100                 105                 110

Cys Arg Val Val Ala Pro Asp Leu Arg Gly His Gly Asp Thr Lys Cys
                115                 120                 125

Ser Asp Glu His Asp Leu Ser Lys Glu Thr Gln Ile Lys Asp Ile Gly
    130                 135                 140

Ala Ile Phe Lys Asn Ile Phe Gly Glu Asp Asp Ser Pro Val Cys Ile
145                 150                 155                 160

Val Gly His Ser Met Gly Gly Ala Leu Ala Ile His Thr Leu Asn Ala
                165                 170                 175

Lys Met Ile Ser Ser Lys Val Ala Ala Leu Ile Val Ile Asp Val Val
                180                 185                 190

Glu Gly Ser Ala Met Glu Ala Leu Gly Gly Met Val His Phe Leu His
                195                 200                 205

Ser Arg Pro Ser Ser Phe Pro Ser Ile Glu Lys Ala Ile His Trp Cys
    210                 215                 220

Leu Ser Ser Gly Thr Ala Arg Asn Pro Thr Ala Ala Arg Val Ser Met
225                 230                 235                 240

Pro Ser Gln Ile Arg Glu Val Ser Glu His Glu Tyr Thr Trp Arg Ile
                245                 250                 255

Asp Leu Thr Thr Thr Glu Gln Tyr Trp Lys Gly Trp Phe Glu Gly Leu
                260                 265                 270

Ser Lys Glu Phe Leu Gly Cys Ser Val Pro Lys Met Leu Val Leu Ala
                275                 280                 285

Gly Val Asp Arg Leu Asp Arg Asp Leu Thr Ile Gly Gln Met Gln Gly
                290                 295                 300
```

```
Lys Phe Gln Thr Cys Val Leu Pro Lys Val Gly His Cys Val Gln Glu
305                 310                 315                 320

Asp Ser Pro Gln Asn Leu Ala Asp Glu Val Gly Arg Phe Ala Cys Arg
                325                 330                 335

His Arg Ile Ala Gln Pro Lys Phe Ser Ala Leu Ala Ser Pro Pro Asp
            340                 345                 350

Pro Ala Ile Leu Glu Tyr Arg Lys Arg His His Gln
            355                 360

<210> SEQ ID NO 8
<211> LENGTH: 2409
<212> TYPE: DNA
<213> ORGANISM: Mus musculus
<220> FEATURE:
<221> NAME/KEY: misc_feature
<222> LOCATION: (1)..(2409)
<223> OTHER INFORMATION: N is A, T, G or C.

<400> SEQUENCE: 8
ttgtactgca cgtatcgtgg gacggacctt gggccactgt tgtcgacgtg cggcctccct      60
ttgatgtcgg cccttgaaaa aagcatgcac ctcggccgcc taccttctcg ccctcctcta     120
cccggcagcg ggggcagtca gagcggacgc aagatgcgga tgggccctgg acggaagcgg     180
gactttaccc ctgtcccatg gagtcagtac tttgagtcaa tggaagatgt ggaagtggag     240
aatgaaactg gcaaggatac ttttcgagtt tacaagattg gttnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnntt cggatccttg gccaagtcaa acagtgtgaa     780
ggaattacaa gtccagaagg ttccaaatcc atagtggaag gaatcataga ggaggaggaa     840
gaagatgagg aaggaagtga gtcagttaac aagaggaaaa aggaagacga catggaaacc     900
aagaaggatc acccatacac ctggagaatt gagctggcaa aaacagaaaa gtactgggat     960
ggctggttcc gggcttatc caatctcttt cttagctgtc ctattcctaa actgctgctc    1020
ttggcgggtg ttgacagatt ggataaagat ctgaccatag gccagatgca gggaagttc    1080 cagatgcagg tcttacccca gtgtggccat gcagtccatg aggatgcccc tgacaaggta    1140
gctgaagctg ttgccacttt cctgatccgg cacaggtttg cagagcccat cggaggattc    1200
cagtgtgtgt ttactggctg ctagtgacct gctgtctact cctccctcta cattgagctc    1260
tgttgtaaat acatcgcacc agaggccact gtgacgccgc tgtctcctcc tctccatccc    1320
gcccagccat gtgacaccgg ctcttgtaga gggcatcccc agatgtccaa accctttcct    1380
gtgtactgtt gaaagcattg ttcttcaggg cccttgtcca acagtggccc gtgcagtctg    1440 ggtccacag ctcttcctct ccttcctgtg ctccctgcct tgcctaggat gaagcctcca    1500
gcgctgctcc ctgccctgt tcctggcata tggcaatgta ccccaggctc agggatctcc    1560
cttccttgag gatgttcttg gcatggtcct gccctacctc atgggatggg caatgcacac    1620
```

-continued

```
actggccctt atttttccct ttcaaataaa acaccagtca ggtaccttta tcccagtctt    1680
aactgtccca aatctggaag gtccagagta agcaggattc agggagaggg agtggatagc    1740
aagtatccca agaaaccaac ctgtaagtca ggtccagcca gtccaagcac atggcttccc    1800
atctgggtga gcccactgtc ccactcccac atgtctgggc acctgccctg ggctgaggcc    1860
aggctgctcc aagggccgca tgagccctaa tctgccacag agcaacccag gttaaacaca    1920
gcccatgcac aaagccacag gctaaatcct gtggaattgt ttttaatgac tgaatttaac    1980
cattttcata gttggttcct ggaggtgtgc caagtgcccg cttgcctctt ctagacccac    2040
agcttcttga tccacttgtg gtttccatgt cactaatgta gaaacatcat ggactagcat    2100
ccccagtctt tgccctcatc cagctgtcgc agcgcacact ggggcctccc cctgctgccc    2160
agggggggrc ggggtgggca gcctcctgaa acccatcttt ctgtgactgt cttaggtgac    2220
gtgtagccct cttccgtttt ttcacccaac aacttcctct gtcctgctgc acggtccaga    2280
gtctgggacc gactttgttt ctttgttatt tatgatcttg tttaaagaaa ataaatatct    2340 cccaacctt aaaaaaaaaa aaaaaaaaa aaaaaaaaaa aaaaaaaaaa aaaaaaaaaa    2400
aaaaaaaaa                                                            2409

<210> SEQ ID NO 9
<211> LENGTH: 1202
<212> TYPE: DNA
<213> ORGANISM: Saccharomyces cerevisiae

<400> SEQUENCE: 9
tgtctgacga tttgagaaga aaaattgctt tatcccagtt tgagagagcc aagaatgttc      60
tagatgcgac attccaagaa gcatacgagg atgatgaaaa cgatggtgat gcattaggtt     120
ccctgccatc atttaatgga caatcaaata ggaacagaaa atatacgggc aaaaccggta     180
gtactactga tagaatttca agtaaggaaa agagtagttt acccacttgg agtgattttt     240
ttgataataa ggagttggta agtcttcctg atagagatct ggacgtaaat acatactata     300
cattacctac ttcattgtta tcaaatacca cttcaattcc catctttatt ttccaccatg     360
gggcgggctc ctcaggttta tcatttgcaa acttggccaa ggaattaaat actaaactag     420
aaggaagatg cggatgcttt gcatttgatg ctaggggca tgcagaaaca agtttaaga      480 aggctgatgc gcctatatgc tttgacaggg actcttttat caaagatttt gtaagcctgc     540
taaattattg gtttaagtct aaaataagcc aagagccact tcagaaggta tctgttatac     600
taattggtca ttcccttggt ggaagtatat gtacttttgc gtaccctaaa ttatcaacag     660
aactacaaaa gaaattcttt ggtattacta tgttagatat tgtagaagag gctgccatta     720
tggccttaaa taaagttgaa cattttttgc agaatacacc caatgtattt gaatcaatta     780
atgacgctgt cgattggcac gttcaacacg cgttatcgag attgaggtca agcgccgaaa     840
ttgctatacc agctttattt gctccgctca gtcagggaa agttgtcagg ataacaaacc     900
ttaagacctt tagcccttc tgggacacat ggtttaccga tctgtcgcac tcctttgttg     960
gcttacctgt tagtaaatta ttaatattgg cgggaaacga aaatctcgat aaagaattaa    1020
ttgtggggca aatgcaaggt aaatatcagt tggtagtttt ccaagattcc gggcatttca    1080
ttcaagaaga ttcgcctata aaaacagcaa tcactttaat tgatttctgg aagcggaacg    1140
attctaggaa tgtagtaatc aagactaatt ggggtcaaca caaaaccgtg caaaatacat    1200
aa                                                                    1202
```

<210> SEQ ID NO 10
<211> LENGTH: 1095
<212> TYPE: DNA
<213> ORGANISM: Caenorhabditis elegans

<400> SEQUENCE: 10

| | | | | | |
|---|---|---|---|---|---|
| atgtccgacg | ataaattaga | cactcttccg | gatcttcaat | cggaaacgtc | acatgtcaca | 60 |
| actcctcaca | ggcaaaatga | tcttcttcgt | caagcggtca | ctcatggaag | gccaccacca | 120 |
| gttccgagca | catcaacttc | tggaaagaaa | cgagaaatgt | ctgaactacc | gtggtcagat | 180 |
| ttttttgatg | aaaagaagga | cgcaaacatt | gatggagatg | ttttcaatgt | gtacataaag | 240 |
| ggaaatgaag | gtccaatttt | ctatttgctt | cacggtggag | gttattcagg | cctcacatgg | 300 |
| gcgtgttttg | cgaaagaatt | ggcaacttta | atatcatgca | gagttgttgc | acctgattta | 360 |
| agaggacacg | gcgacactaa | atgttctgat | gagcacgatc | tttcgaaaga | aacccaaata | 420 |
| aacgatattg | gagcaatctt | caagaacatt | ttcggcgaag | acgattcacc | agtatgcatt | 480 |
| gttggacaca | gtatgggtgg | tgcattggcc | attcatacat | gaatgcaaa | gatgatttct | 540 |
| tcaaaagtcg | ctgcactcat | tgtcattgat | gttgtcgaag | gttccgctat | ggaagcactt | 600 |
| ggaggaatgg | ttcatttttt | acattcaagg | ccttcttcat | ttccttctat | cgaaaaagcc | 660 |
| attcactggt | gcctttcttc | gggtacagcg | aggaatccca | cagctgcacg | ggtctcaatg | 720 |
| ccgtctcaaa | ttagagaagt | atcggaacac | gagtacactt | ggcgaattga | tttaacaaca | 780 |
| acagaacagt | actggaaagg | atggtttgaa | ggattatcca | agaattttt | gggatgttcc | 840 |
| gttccgaaga | tgcttgttct | agcgggcgtt | gatcggctgg | acagggatct | cacaattggt | 900 |
| caaatgcagg | aaagtttca | gacttgtgtg | ttaccaaaag | ttggacattg | tgttcaggaa | 960 |
| gatagcccac | aaaatcttgc | agatgaagtc | ggaagattcg | cttgccgcca | tagaattgcc | 1020 |
| caaccgaaat | tctcagccct | tgcatcacca | ccagatccag | cgattctcga | atacagaaaa | 1080 |
| cgtcatcacc | aataa | | | | | 1095 |

<210> SEQ ID NO 11
<211> LENGTH: 9
<212> TYPE: PRT
<213> ORGANISM: Homo sapiens

<400> SEQUENCE: 11

Ile Met Leu Ile Gly His Ser Met Gly
 1               5

<210> SEQ ID NO 12
<211> LENGTH: 9
<212> TYPE: PRT
<213> ORGANISM: Caenorhabditis elegans

<400> SEQUENCE: 12

Val Cys Ile Val Gly His Ser Met Gly
 1               5

<210> SEQ ID NO 13
<211> LENGTH: 9
<212> TYPE: PRT
<213> ORGANISM: Saccharomyces cerevisiae

<400> SEQUENCE: 13

Val Ile Leu Ile Gly His Ser Leu Gly
 1               5

```
<210> SEQ ID NO 14
<211> LENGTH: 9
<212> TYPE: PRT
<213> ORGANISM: Salmonella typhimurium

<400> SEQUENCE: 14

Leu Ile Ala Ile Gly Ala Ser Thr Gly
 1               5

<210> SEQ ID NO 15
<211> LENGTH: 10
<212> TYPE: PRT
<213> ORGANISM: Artificial sequence
<220> FEATURE:
<221> NAME/KEY: UNSURE
<222> LOCATION: (1)
<223> OTHER INFORMATION: X at position 1 is Leu, Ile or Val.
<223> OTHER INFORMATION: Description of Artificial Sequence: Signature
      motif for lipases.
<221> NAME/KEY: UNSURE
<222> LOCATION: (2)
<223> OTHER INFORMATION: X at position 2 is not specified as a
      particular amino acid.
<221> NAME/KEY: UNSURE
<222> LOCATION: (3)
<223> OTHER INFORMATION: X at position 3 is Leu, Ile, Val, Phe or Tyr.
<221> NAME/KEY: UNSURE
<222> LOCATION: (4)
<223> OTHER INFORMATION: X at position 4 is Leu, Ile, Val, Ser or Thr.
<221> NAME/KEY: UNSURE
<222> LOCATION: (6)
<223> OTHER INFORMATION: X at position 6 is His, Tyr, Trp or Val.
<221> NAME/KEY: UNSURE
<222> LOCATION: (8)
<223> OTHER INFORMATION: X at position 8 is not specified as a
      particular amino acid.
<221> NAME/KEY: UNSURE
<222> LOCATION: (10)
<223> OTHER INFORMATION: X at position 10 is Gly, Ser, Thr, Ala or Cys.

<400> SEQUENCE: 15

Xaa Xaa Xaa Xaa Gly Xaa Ser Xaa Gly Xaa
 1               5                  10

<210> SEQ ID NO 16
<211> LENGTH: 51
<212> TYPE: DNA
<213> ORGANISM: Homo sapiens

<400> SEQUENCE: 16
tgactacgtg cgtgcagcct cccctcgatg tcggccctcg aaaagagcat g          51

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Sequence
      resulting from alternative splicing.

<400> SEQUENCE: 17

Leu Leu Ser Thr Tyr Cys Arg
 1               5
```